United States Patent
Walker et al.

(10) Patent No.: US 7,601,886 B2
(45) Date of Patent: Oct. 13, 2009

(54) PRODUCTION OF TRANSGENIC PLANTS WITH INCREASED SEED YIELD

(75) Inventors: John C. Walker, Columbia, MO (US); Jiangqi Wen, Ardmore, OK (US); Jia Li, Norman, OK (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 11/198,886

(22) Filed: Aug. 5, 2005

(65) Prior Publication Data

US 2006/0085872 A1  Apr. 20, 2006

Related U.S. Application Data

(60) Provisional application No. 60/599,378, filed on Aug. 6, 2004.

(51) Int. Cl.
*C12N 15/09* (2006.01)
*C12N 15/82* (2006.01)
*A01H 1/00* (2006.01)

(52) U.S. Cl. .................. 800/278; 800/298; 800/295; 800/287; 800/267; 435/468

(58) Field of Classification Search .................. None
See application file for complete search history.

(56) References Cited

OTHER PUBLICATIONS

Venter, J.C. Nature (1999) 402:761-768.*
Fourgoux-Nicol et al (1999), Plant Molecular Biology 40: 857-872.*
Accession No. A29639, (1999).
Accession No. AAC63668.1, (2002).
Accession No. AAC63669.1, (2002).
Accession No. AAF21209.1, (2002).
Accession No. AAG13597, (2001).
Accession No. AAG46107.1, (2001).
Accession No. AAK44013.1, (2001).
Accession No. AAM65590.1, (2006).
Accession No. AAM65698.1, (2006).
Accession No. AAN86167.1, (2002).
Accession No. AAO11573.1, (2002).
Accession No. AAQ63884, (2003).
Accession No. AC051633, (2001).
Accession No. AJ251969, (2005).
Accession No. AK111801, (2003).
Accession No. AK111818, (2003).
Accession No. AP004069, (2004).
Accession No. AY308957, (2003).
Accession No. BAB64666.1, (2004).
Accession No. BAD19260, (2004).
Accession No. BAD19262, (2004).
Accession No. BAD25094, (2004).
Accession No. CAA70815.1, (2005).
Accession No. CAC19488, (2005).
Accession No. NM_184451, (2004).
Accession No. NM_190464, (2004).
Accession No. NM_197584, (2004).
Accession No. NP_909340, (2004).
Accession No. NP_915353, (2004).
Accession No. NP_922566, (2004).
Accession No. P08818, (2006).
Accession No. P55748, (2006).
Accession No. T05701, (2000).
Accession No. X78878, (2005).
Accession No. Y09602, (2005).
Barr, PJ.,"Mammalian subtilisins: the long-sought dibasic processing endoproteases," *Cell*, 66:1-3, 1991.
Berger and Altmann, "Subtilisin-like serine protease involved in the regulation of stomatal density and distribution in *Arabidopsis thaliana*," *Genes Dev.*, 14:1119-1131, 2000.
Dmochowska et al., "Yeast KEX1 gene encodes a putative protease with a carboxypeptidase B-like function involved in killer toxin and alpha-factor precursor processing," *Cell*, 50:573-584, 1987.
Friedrichsen et al., "Brassinosteriod-insensitive-1 is a ubiquitously expressed leucine-rich repeat receptor serine/threonine kinase," *Plant Physiol.*, 123:1247-1256, 2000.
Jinn et al., "HAESA, an Arabidopsis leucine-rich repeat receptor kinase, controls floral organ abscission," *Genes Dev.*, 14:108-117, 2000.
Lehfeldt et al., "Cloning of the SNG1 gene of Arabidopsis reveals a role for a serine carboxypeptidase-like protein as an acyltransferase in secondary metabolism," *Plant Cell*, 12:1295-1306, 2000.
Li and Chory, "A putative leucine-rich repeat receptor kinase involved in brassinosteriod signal transduction," *Cell*, 90:929-938, 1997.
Li and Steffens, "An acyltransferase catalyzing the formation of diacylglucose is a serine carboxypeptidase-like protein," *Proc. Natl. Acad. Sci. USA*, 97:6902-6907, 2000.
Li et al., "A role for brassinosteriods in light-dependant dependant development of Arabidopsis," *Science*, 272:398-401, 1996.
Li et al., "BRS1, a serine carboxypeptidase, regulates BRII signaling in *Arabidopsis thaliana*," *Proc. Natl. Acad. Sci. USA*, 98:5916-5921, 2001.
Li et al., "Kinase interaction domain of kinase-associated protein phosphatase, a phosphoprotein-binding domain," *Proc. Natl. Acad. Sci. USA*, 96:7821-7826, 1999.
Neuteboom et al., "Isolation and characterization of cDNA clones corresponding with mRNAs that accumulate during auxin-induced lateral root formation," *Plant Mol. Biol.*, 39:273-287, 1999.
Schaller and Ryan, "Identification of a 50-kDa systemin-binding protein in tomato plasma membranes having Kex2p-like properties," *Proc. Natl. Acad. Sci. USA*, 91:11802-11806, 1994.
Tornero et al., "Characterization of LRP, a leucine-rich repeat (LRR) protein from tomato plants that is processed during pathogenesis," *Plant J.*, 10:315-330, 1996.
Walker et al., "DNA sequences required for anaerobic expression of the maize alcohol dehydrogenase 1 gene," *Proc. Natl. Acad. Sci. USA*, 84:6624-6628, 1987.

\* cited by examiner

*Primary Examiner*—Medina A Ibrahim
(74) *Attorney, Agent, or Firm*—Fulbright & Jaworski, LLP

(57) ABSTRACT

The invention provides methods of producing plants with increased seed production and transgenic plants with increased seed yields produced by said methods.

11 Claims, 5 Drawing Sheets

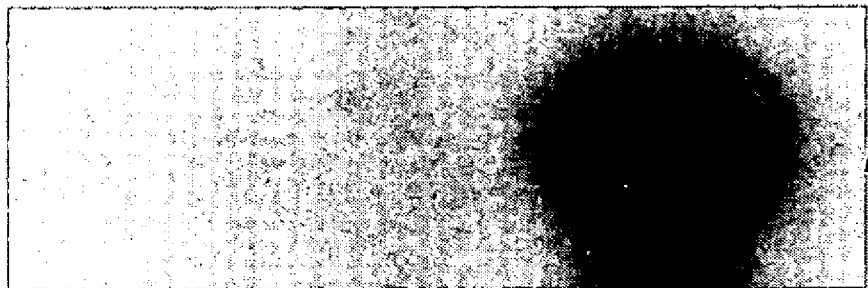
FIG. 1

```
ECS1       MARTHL-LFLLFV-LLSLA-----TSSTSTKEQEEDRIKALPGQP-KVGFSQFSGYVTVNESHGRSLFYWLTESS-SHSPHTKPL   76
BRS1       MARTHF-IFLLLVALLSTT----FPSSSSSREQEKDRIKALPGQP-KVAFSQYSGYVNVNQSHGRALFYWLTESS-SPSPHTKPL   78
Homolog1   M-------------------------------------IKALPGQP-QVGFSQFSGYVTVNESHGRSLFYWLTESP-S-SSHTKPL   46
Homolog2   MAMAKLAIFTTLMAILVMTSQGRIPTEGGEKEAEADRITSLPGQP-NVTFEDFSGYVTVDKLSGRSLFYWLTEAS-DL-PLSKPL   82
Homolog3   MARIL-LLFFFDILLHYASCSR-------HEQEKDRIFHLPGEPNDVSFSHFSGYITVNESAGRALFYWLIESPPSENPESKPL   77
Homolog4   MDYS-FLLIILLLTI-SISCCAA---PSSYVEEQLRDRISNLPGQPSNVDFRQYSGYVTVHEERGRALFYWLVESPLARDFKSRPL   81

ECS1       LLWLNGGPGCSSIAYGASEEIGPFRISKTGCNLYLNNFSWNTEANLLFLESPVGVGFSYTNTSSDFEESGDERTAQENLIFLISW   161
BRS1       LLWLNGGPGCSSIAYGASEEIGPFRINKTGSNLYLNKFAWNKDANLLFLESPAGVGYSYTNTSSDLKDSGDERTAQDNLIFLIKW   163
Homolog1   LLWLNGGPGCSSLGYASEEIGPFRINKTGSNLYLNKFTWNTEANILFLESPAGVGFSYTNTSSDLKDSGDERTAQENLIFLIKW   131
Homolog2   VIWLNGGPGCSSVAYGASEEIGPFRISKGGSGLYLNKFAWNSISNLLFLEAPAGVGFSYITNRSSDLFNTGDRRTAKDSLQFLIQW   167
Homolog3   VLWLNGGPGCSSVAYGAEEIGPFRINPDGKTLYHNPYSWNKLANLLFLESPAGVGFSYSNTTSDLYTAGDQRTAEDAYVFLVKW   162
Homolog4   VLWLNGGPGCSSVAYGAAEEIGPFRVGSDGKTLHSKLYAWNKLANLLFLESPAGVGFSYSNTTSDLYTTGDQRTAEDSYIFLVNW   166

ECS1       MSRFPQYRYRDFYIVGESYAGHYVPQLAQKIHEYNNAYKN-PVINLKGFMVGNPEMDKNNDRLGTITYWWSHAMISDASYNRILK    245
BRS1       LSRFPQYKYRDFYIAGESYAGHYVPQLAKKINDYNKAFSK-PIINLKGFLVGNAVTDNQYDSIGTIVIYWWTHALISDKSYKSLLK    247
Homolog1   MSRFPQYQYRDFYIVGESYAGHYVPQLAKKIHLYNKAFNNTPILNLKGFMVGNGDMDKHYDRLGAAMYAWSHAMISDKTYKSLLK   216
Homolog2   LHRFPRYNHRELYITGESYAGHYVPQLAKELMNYNK--RSKNPLNLKGIMVGNAVTDNHYDNLGTIVSYWWSHAMISDRTYHQLIS   250
Homolog3   FERFPQYKHREFYIAGESYAGHYVPQLSQIVYEK----RN-PAINFKGFIVGNAVIDDYHDYVGLFEYWWAHGLISDLTYHNLRI    242
Homolog4   FERFPQYKHREFYIVGESYAGHFVPQLSKLVHERNKGFKN-PAINLKGFMVGNAVTDDYHDYIGTFEYWWNHGLISDSTYHQLKT    250

ECS1       NCDF-IADRFSKFCDSAI-YVAAADFGDIDQYSIYTPKCVPPQDQT----NQTKFEQMMQM-HTTKRFLEDQY--DPCTENYAELY   322
BRS1       YCNF-TVERVSDDCDNAVNYAMNHEFGDIDQYSIYTPTCVAAQQKK---NTIGFFVRLKN-TLLRRRLVSGY--DPCTESYAEKY   325
Homolog1   HCSF-LADKTSDKCNWAL-YFAYREFGKVNGYSIYSPSCV---HQT---NQTKF-----L-HG--RLLVEEMEYDPCTESYAELY   285
Homolog2   TCDF-SRQKESDECETLYSYAMEQEFGNIDQYNIYAPPCNKSSDGGGSYNGSSGRRSNRLPHLPHSVLRKISGYDPCTERYAELY   334
Homolog3   TCEFGSSEHPSSKCTKAME-AADLEQGNIDPYSIYTVTC-----KKEAAALRSRFSRVRHPWMWR-------AYDPCTEKYSGMY   314
Homolog4   ACYSVSSQHPSMQCMVALR-NAELEQGNIDPYSIFLKPC-----NS-TVALK-RFLKGRYPWMSR-------AYDPCTERYSNVY   320

ECS1       YNRPEVQRAMHANHTAIPYKWIACSDSVFNNWNWRDSDNSMLPIYKELLAAGLRIWVYSGDTDSVLPVTATRYSLGKLNLRVKTR   407
BRS1       FNRPDVQRAMHANVIGIRYKWIACSDVLIKTW--KDSDKTMLPIYKELAASGLRIWIFSGDTDSVVPVTATRFSLSHLNLPVKTR   408
Homolog1   YNRPDVQRAMHANLISIPYKWILCNMVVNNN--WKDSEFSMLPIYKELTAAGLRIWVFSGDTDAVYPVTGTRLALSKLNLPVKIP   368
Homolog2   YNRPDVQKALHANTTKIPYKWIACSEVL--NRNWNDIDSTVLPIYREMIAGGIRVWVFSGDVDSVVPVTATRYSLARLSLSTKLP   417
Homolog3   FNSPEVQKAMHANIIGLAVPWKGCSDIVGEK--WADSPLSMLPIYKELIIAGLKLWVFSGDTDSVPITGIRYSIRALKLQPLSK   397
Homolog4   FNRLDVQKALHANVIRLSVPWKACSDIVGSY--WDDSPLSMLPIYKELIITAGLKLWVFSGDTDAVVPITATRYSVDALKLATILN   403

ECS1       WYPWYSGNQVGGRTEVYYEGLTFVVRGAGHEVPFFQPQSALILLRSFLAGNELSRSY                                   464
BRS1       WYPWYTDNQVGGWIEVYKGLTFATVRGAGHEVPLFEPKRALILFRSFLAGKELPRSY                                   465
Homolog1   WYPWYSEKQVGGWIEVYEGLTFAIIRGAGHEVPVLQPERALTLLRSFLAGKELPRSY                                   425
Homolog2   WYPWYVKKQVGGWIEVYYEGLTFVVRGAGHEVPLFKPRAAFELFKYFLRGKPLPKA                                    473
Homolog3   WYPWNDDGQVGGWSQVYKGLTLVTLHGAGHEVPLFRPRRAFLLFQSFLDNKPLPM                                     452
Homolog4   WYPWYDHGKVGGWSQVYKGLTLVTVAGAGHEVPLHRPRQAFILFRSFLESKPMPMT                                    459
```

PRODUCTION OF TRANSGENIC PLANTS WITH INCREASED SEED YIELD

This application claims the priority of U.S. Provisional Patent Appl. Ser. No. 60/599,378, filed Aug. 6, 2004, the entire disclosure of which is specifically incorporated herein by reference.

BACKGROUND OF THE INVENTION

1. Field of the Invention

The present invention relates generally to the field of molecular biology. More specifically, the invention relates to methods and compositions for increasing plant seed yield.

2. Description of the Related Art

BRS1 is a secreted serine carboxypeptidase that is implicated in an early step in brassinosteroid signaling, probably by taking part in the proteolytic processing of a protein involved in activating the BRI1 receptor (Li et al., 2001). The protease activity of BRS1 is required for its function in suppressing the phenotypes of a weak BRI1 allele, bri1-5. BRI1 is a member of a serine carboxypeptidase gene family in *Arabidopsis*. The fact that a loss-of-function allele of BRS1 does not show any significant phenotypes suggests that there is functional redundancy among the family members.

It has been shown that BRS1 overexpression suppresses multiple bri1 defects, suggesting BRS1 might play an important role in an early stage of the BRI1 signaling pathway (Li et al., 2001). The presence of an N-terminal signal peptide in BRS1 predicts that the protein should enter the secretory pathway. Sequence analysis failed to identify any obvious endoplasmic reticulum or Golgi apparatus retention sequences. Therefore, BRS1 may be a secreted protein. These observations are consistent with findings that BRS1 suppressed two extracellular domain mutants, bri1-5 and bri1-9, but failed to suppress a loss-of-function cytoplasmic domain mutant bri1-1 (Friedrichsen et al., 2000).

BRS1 shares homology with another serine carboxypeptidase II-like protein, designated ECS1. Like BRS1, ECS1 is predicted to have an N-terminal signal peptide and should be secreted. Based on its biochemical properties, yeast Kex1p is classified in the same carboxypeptidase group (carboxypeptidase D). In yeast, both Kex1p and Kex2p/kexin are required for the maturation of peptide hormones, α-mating pheromone and K1 killer toxin, from their inactive precursors (Dmochowska et al., 1987; Fuller, 1989). Kex2p/kexin is a membrane bound endoprotease, which specifically cleaves on the carboxyl side of pairs of basic amino acids (e.g. KR↓ or RR↓). Kex2p related endoproteases are also known as subtilisin and furin (Barr, 1991). Following the action of Kex2p/Kexin, Kex1p selectively trims off the flanking amino acids from the C-terminus of processing intermediates.

There are numerous examples of the importance of carboxypeptidases in ligand processing in animals. For example, a mutation in carboxypeptidase E (CPE), a metallopeptidase, results in the fat mouse mutant (Naggert et al., 1995; Fricker and Leiter, 1999). CPE is widely distributed in brain, pituitary and other neuroendocrine tissues and is thought to be involved in the processing the precursors of neuroendocrine peptides (Naggert et al., 1995; Fricker and Leiter, 1999).

In addition to ligand processing, there are also examples of receptor proteolytic processing. One example of receptor processing is the insulin receptor. Both insulin and insulin receptor are synthesized as inactive precursors. Proinsulin and insulin proreceptors are processed by furin-like endoproteases in the trans Golgi network to form active molecules, which recognize and cleave at the carboxy terminal sites of dibasic amino acids. Proinsulin is processed at the C-termini of KR and KTRR sites. The insulin proreceptor is processed at the RKRR site (Barr, 19991).

In plants, there are a few reports concerning the processing of ligand-like peptides or receptor-like proteins. In response to wounding, tomato systemin is processed from its inactive form, preprosystemin (Schaller and Ryan, 1994). Also in tomato, a secreted leucine-rich repeat protein (LRP), which was thought to be involved in a plant defense response, is proteolytically processed during pathogenesis (Tornero et al., 1996). It is not clear whether prosystemin is cleaved by a subtilisin-like endoprotease, but it has been found that systemin physically interacts with a subtilisin-like protein SPB50 (Schaller and Ryan, 1994). LRP is likely to be processed by a subtilisin/Kex2p-like endoprotease (Tornero et al., 1996). Additionally, the functions of two *Arabidopsis* Kex2p-like genes have been determined: AIR3 is involved in the regulation of auxin-induced lateral root formation (Neuteboom et al., 1999) and SDD1 functions in guard cell development (Berger and Altmann, 2000).

The regulatory roles of serine carboxypeptidases in plants have not yet been investigated. Therefore, while the foregoing studies have further understanding of plant metabolism, a beneficial use for numerous serine carboxypeptidases and for ECS1 and its orthologs in particular has been lacking.

SUMMARY OF THE INVENTION

In one aspect, the invention provides a transgenic plant expressing a selected DNA conferring increased seed production and/or yield to the plant relative to a second plant of the same genotype lacking the selected DNA. In certain embodiments of the invention, the selected DNA comprises the nucleic acid sequence of SEQ ID NO:3, SEQ ID NO:5, SEQ ID NO:7; SEQ ID NO:9; SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 or SEQ ID NO:32. In another embodiment, the selected DNA encodes a polypeptide selected from the group consisting of SEQ ID NO:4, SEQ ID NO:6, SEQ ID NO:8; SEQ ID NO:10; SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31 and SEQ ID NO:33. In still another embodiment, the selected DNA is further defined as hybridizing to the nucleic acid sequence of SEQ ID NO:3, SEQ ID NO:5, SEQ ID NO:7; SEQ ID NO:9; SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 or SEQ ID NO:32 under conditions of 5×SSC, 50% formamide and 42° C. In still another embodiment, the selected DNA is further defined as encoding a polypeptide comprising at least 90% amino acid identity to a sequence selected from the group consisting of SEQ ID NO:4, SEQ ID NO:6, SEQ ID NO:8; SEQ ID NO:10; SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31 and SEQ ID NO:33.

A transgenic plant provided by the invention may comprise a selected DNA operably linked to a heterologous promoter. Such a promoter may be, for example, a developmentally-regulated, organelle-specific, inducible, tissue-specific, constitutive, cell-specific, seed specific, or germination-specific promoter. In certain embodiments, the selected DNA further comprises at least one additional sequence chosen from the group consisting of: a regulatory sequence, a selectable or screenable marker, a leader sequence and a terminator. The transgenic plant may be further defined as a monocotyledonous plant. Examples of such plants include wheat, maize, rye, rice, oat, barley, sorghum or millet. The plant may further be a dicotyledonous plant. Examples of such plants include a tomato, potato, soybean, canola, alfalfa, pea or sunflower. The transgenic plant may further be defined as a progeny plant of any generation of an $R_0$ transgenic plant, wherein the transgenic plant has inherited the selected DNA from the $R_0$ transgenic plant.

The invention also provides parts of a transgenic plant of the invention. In one embodiment such a part is a seed, wherein the seed comprises the selected DNA. A cell of a plant of the invention is also provided. Such a cell may be defined as expressing a protein encoded by the selected DNA. The cell may have inherited the selected DNA from a progenitor of the cell, and may have been transformed with the selected DNA.

In another aspect, the invention provides a transformation construct comprising an isolated nucleic acid sequence encoding a polypeptide having at least 90% amino acid identity to a polypeptide selected from the group consisting of SEQ ID NO:4, SEQ ID NO:6, SEQ ID NO:8; SEQ ID NO:10; SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31 and SEQ ID NO:33, wherein the isolated nucleic acid sequence is operably linked to a heterologous promoter. The isolated nucleic acid sequence may be further defined as comprising the nucleic acid sequence of SEQ ID NO:3, SEQ ID NO:5, SEQ ID NO:7; SEQ ID NO:9; SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 or SEQ ID NO:32. In further embodiments, the isolated nucleic acid sequence may encode a polypeptide selected from the group consisting of SEQ ID NO:4, SEQ ID NO:6, SEQ ID NO:8; SEQ ID NO:10; SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31 and SEQ ID NO:33. In still further embodiments, the isolated nucleic acid sequence may hybridize to the nucleic acid sequence of SEQ ID NO:3, SEQ ID NO:5, SEQ ID NO:7; SEQ ID NO:9; SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 or SEQ ID NO:32 under conditions of 5×SSC, 50% formamide and 42° C. The heterologous promoter may, for example, be a developmentally-regulated, organelle-specific, inducible, tissue-specific, constitutive, cell-specific, seed specific, or germination-specific promoter. A nucleic acid provided by the invention may defined, for example, as having at least 70%, 80%, 85%, 90%, 95%, 98%, 99% or more sequence identity to one or more nucleic acid sequence(s) selected from SEQ ID NO:3, SEQ ID NO:5, SEQ ID NO:7; SEQ ID NO:9; SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 or SEQ ID NO:32.

In yet another aspect, the invention provides a method for increasing seed production and/or yield in a plant comprising introducing into the plant a nucleic acid sequence selected from the group consisting of: (a) the nucleic acid sequence of SEQ ID NO:3, SEQ ID NO:5, SEQ ID NO:7; SEQ ID NO:9; SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 or SEQ ID NO:32; (b) a nucleic acid sequence encoding the polypeptide of SEQ ID NO:4, SEQ ID NO:6, SEQ ID NO:8; SEQ ID NO:10; SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31 or SEQ ID NO:33; (c) a nucleic acid sequence defined as hybridizing to the nucleic acid sequence of SEQ ID NO:3, SEQ ID NO:5, SEQ ID NO:7; SEQ ID NO:9; SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 or SEQ ID NO:32 under conditions of 5×SSC, 50% formamide and 42° C.; and (d) a nucleic acid sequence encoding a polypeptide comprising at least 90% amino acid identity to the polypeptide sequence of SEQ ID NO:4, SEQ ID NO:6, SEQ ID NO:8; SEQ ID NO:10; SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31 or SEQ ID NO:33.

In a method of the invention, the isolated nucleic acid sequence may be defined as from a species selected from the group consisting of: *Arabidopsis thaliana,* barley, potato, rice, pea, tomato, wheat and alfalfa. In such a method the number of seed produced by the plant may be increased relative to a second plant of the same genotype lacking the isolated nucleic acid and/or the weight of seed produced by the plant may be increased relative to a second plant of the same genotype lacking the isolated nucleic acid. Introducing the isolated nucleic acid may comprise plant breeding and may comprise genetic transformation.

In still yet another aspect, the invention provides a method of making food for human or animal consumption comprising: (a) obtaining a plant of the invention: (b) growing the plant under plant growth conditions to produce plant tissue from the plant; and (c) preparing food for human or animal consumption from the plant tissue. In the method preparing food may comprise harvesting the plant tissue. The food may be starch, protein, meal, flour or grain.

In still yet another aspect, the invention provides a method of preparing seed comprising: (a) obtaining a plant of the invention; (b) growing the plant under plant growth conditions to produce seed; and (c) collecting seed produced by the plant.

The use of the word "a" or "an" when used in conjunction with the term "comprising" in the claims and/or the specification may mean "one," but it is also consistent with and encompasses the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1. Overexpression of ECS1 in wildtype *Arabidopsis*. Both Columbia and WS ecotypes express a very low level of ECS1, while the ECS1-overexpressing line (in WS background) has an elevated ECS1 expression level (top panel). ACT7 was used as a probe to show the sample equal loading of total RNA (bottom panel).

FIG. 4. Alignment of the predicted amino acid sequence of ECS1 (SEQ ID NO:2) with the predicted amino acid sequences of the five most related genes in *Arabidopsis thaliana*. Amino acids that match ECS1 are shaded in black. Note that Homologue 1 lacks an N terminal signal sequence.

FIG. 5. Alignment of the predicted amino acid sequence of *Arabidopsis* ECS1 (SEQ ID NO:2) with the predicted amino acid sequences of the four most related genes in rice and barley (SEQ ID NO:8). Amino acids that match ECS1 are shaded in black. Note that rice Homologue 2 is identical to rice Homologue 1 except it lacks the N-terminal signal sequence as seen in rice Homologue 1. The Rice ECS1, Rice ECS1/H1 and Rice ECS1/H2 sequences correspond to Rice ECS1 Homolog 2, Homolog 5 and Homolog 6, respectively (SEQ ID Nos:25, 31 and 33).

DETAILED DESCRIPTION OF THE INVENTION

Figure 2:
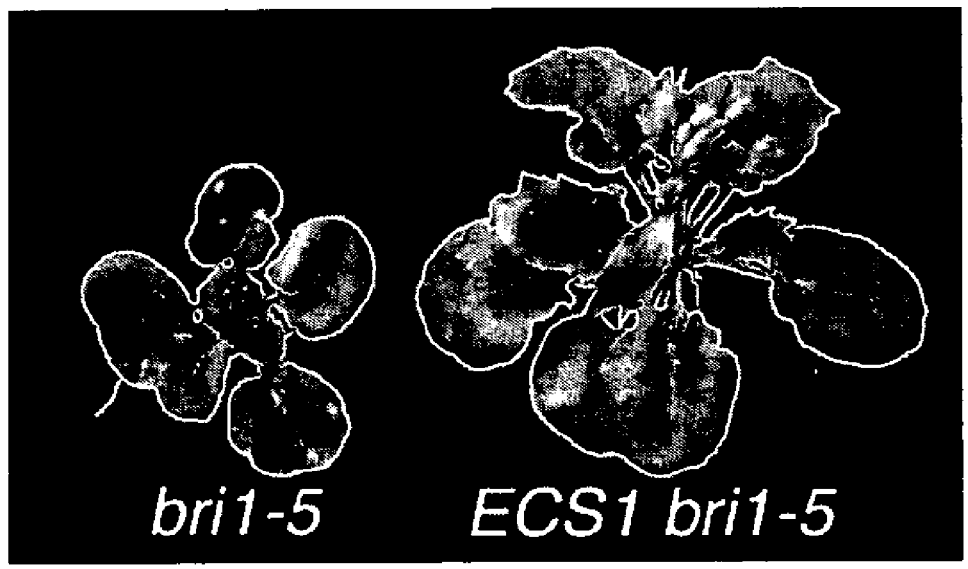
FIG. 2. Overexpression of ECS1 suppresses bri1-5 phenotypes. Rosette leaves in BRI1-5 are curled, while ECS1-overexpressing plants have expanded leaves. bri1-5 plants flower 7-10 days later than wildtype plants, while ECS1-overexpressing plants flower 5-7 days earlier than bri1-5 plant.

The invention overcomes the limitations of the prior art by providing isolated nucleic acids conferring increased seed production in plants. In accordance with the invention, the nucleic acids may be introduced into selected plant species to increase seed yield. This may be achieved, for example, using developmentally-regulated promoters, or using constitutive or other desired regulatory elements.

The inventors demonstrated that heterologous overexpression of a gene designated ECS1 under a strong constitutive promoter increased the numbers of carpels and seeds per silique. Wildtype Arabidopsis plants have two carpels. In contrast, ECS1-overexpressing lines had three carpels, although some siliques had four carpels. Wild type plants have an average seed number of 66.2 seed/silique, whereas ECS1-overexpressing lines have 88.1 seeds per silique. The invention is therefore significant in that it may be used to increase seed production in a variety of crop species.

The ECS1 gene was first identified via its homology with a BRI1 (brassinosteroid-insensitive 1) suppressor, BRS1 (bri1 suppressor 1). BRS1 encodes a secreted serine carboxypeptidase that is implicated in an early step in brassinosteroid signaling, probably by taking part in the proteolytic processing of a protein involved in activating the BRI1 receptor (Li et al., 2001). The protease activity of BRS1 is required for its function in suppressing the phenotypes of a weak BRI1 allele, bri1-5.

BRS1 is a member of a serine carboxypeptidase gene family in *Arabidopsis*. The fact that a loss-of-function allele of BRS1 does not show any significant phenotypes suggested there is functional redundancy among the family members. To test if other members of the gene family play similar roles in suppressing the phenotypes of bri1-5, five closely related homologues of BRS1 were chosen and overexpressed. Three out of the five BRS1-related genes suppressed the phenotypes of bri1-5 allele. Among these three homologues, ECS1 produced an additional phenotype, i.e., increases in the numbers of carpels and seeds as described herein below.

Database searching was carried out to reveal orthologous ECS1 sequences in *Arabidopsis*, rice, barley, pea, Medicago. The sequence listing numbers of ECS1 and homologous and orthologous sequences are listed in Table 1. The five most closely related *Arabidopsis* sequences were aligned with ECS1 as shown in FIG. 4. ECS1 was 72% identical to BRS1 at the amino acid sequence level. The homologies between ECS1 and homologues 2-4 range from 52% to 60%. The homologies in the middle part of these proteins are lower than those of N-terminal and C-terminal parts. It is worth noting that homolog 1 shares 75% identity to ECS1 but lacks a N-terminal signal peptide. Interestingly, overexpression of *Arabidopsis* ECS1 homologue 1 does not suppress the bri1-5 defects and does not have the ECS1 extra-carpel silique phenotype.

The homology between ECS1, BRS1 and other type II serine carboxypeptidases indicated that ECS1 is a serine carboxypeptidase II-like protein. In addition, like BRS1, ECS1 was predicted to have an N terminal signal peptide and should be secreted. Based on its biochemical properties, yeast Kex1p is classified in the same carboxypeptidase group (carboxypeptidase D).

The regulatory roles of serine carboxypeptidases in plants have not yet been investigated. Based on an analogy with BRS1, it was predicted, without limitation to any particular mode of action, that ECS1 either process an unidentified proteinaceous proligand or a cell surface receptor (BRI1 or a BRI1 related receptor) that is involved in the control of carpel development. This processing may resemble the actions of yeast Kex1p and Kex2p, in which an *Arabidopsis* Kex2p-like endoprotease may recognize and cleave a dibasic site in its substrate. Following the cleavage, ECS1 further trims the processing intermediate, releasing either an active (co-) ligand or a functional receptor. The processing step by ECS1 may be rate limiting. Thus, elevated expression of ECS1 can increase the amount of the active form of the ligand or receptor, which subsequently enhances the signal transduction pathway involved in carpel development. As a result, extra carpels are formed and the number of seed increases.

The currently available approaches to increase seed production include traditional breeding practice (including generating hybrid plants with higher yields) and eliminating factors that reduce seed production (e.g., increasing plant's disease resistance and tolerance to various stress stimuli). It has not been shown that overexpression of the ECS1 gene, or genes that encode related carboxypeptidases, produces an increase in carpel and seed numbers in any plants.

Seed production is an essential component of crop yield. Increasing seed production has long been a pursuit of crop breeders. The invention provides a novel approach to increase seed production. After obtaining the desirable transgenic plants (i.e., plants that overexpress ECS1, its homologues or its orthologs and have been shown to have higher seed production), one can simply plant the seeds obtained from the transgenic plants without any additional manipulations. It is advantageous over traditional breeding practice, which is time-consuming and labor-intensive. Certain breeding practices require constant hybridization of desirable parent lines before seeds from hybrid plants are planted. The instant approach is also more widely applicable over those that eliminate a particular factor that reduces seed production. The transgenic plants according to the present invention may be additionally engineered with other traits such as increased disease resistance or tolerance to cold stress that further increase their seed production. The invention may be used in agriculture to increase seed production of potentially any economically valuable plants, including, for example, soybean, *Brassica napus* (Canola/rape), rice, maize, barley, etc.

I. Plant Transformation Constructs

In one embodiment of the invention, plant transformation constructs are provided encoding one or more ECS1 coding sequence. By an "ECS1" sequence it is meant the nucleic acid sequences described herein capable of conferring increased seed production in plants as well as the polypeptides encoded by these sequences. Increased seed yield refers to an increase in the number of seeds and/or weight of seeds produced by a plant relative to a plant lacking a particular heterologous ECS1 coding sequence. An exemplary coding sequence for use with the invention is an *Arabidopsis thaliana* ECS1 sequence encoding the polypeptide sequence of SEQ ID NO:2. Such a coding sequence may comprise the nucleic acid sequence of SEQ ID NO:1.

Also provided by the invention are constructs encoding homologs and orthologs of the ECS1 coding sequences from both *Arabidopsis* and other plants. In certain embodiments of the invention, the orthologous sequences are from rice, barley, wheat, pea, Medicago, and *Arabidopsis*. Examples of such nucleic acids are given in SEQ ID NO:3, SEQ ID NO:5, SEQ ID NO:7; SEQ ID NO:9; SEQ ID NO:11, SEQ ID NO:12, SEQ ID NO:14, SEQ ID NO:16, SEQ ID NO:18, SEQ ID NO:20 and SEQ ID NO:22. Such nucleic acids may be further characterized as encoding a polypeptide sequence selected from the group consisting of SEQ ID NO:4, SEQ ID NO:6, SEQ ID NO:8; SEQ ID NO:10; SEQ ID NO:13, SEQ ID NO:15, SEQ ID NO:17, SEQ ID NO:19, SEQ ID NO:21 and SEQ ID NO:23.

One embodiment of the invention therefore provides a recombinant vector comprising one or more of the foregoing sequences, including all possible combinations thereof, as well as plants transformed with these sequences. Also provided by the invention are nucleic acids encoding the polypeptides encoded by these sequences, as well as polypeptides having at least about 85%, 90%, 95%, 98% and 99% amino acid identity to these sequences.

Nucleic acids that hybridize under stringent conditions to the coding sequences described herein and the use of such sequences are also provided by the invention. An example of these conditions is 5×SSC, 50% formamide and 42° C. It will be understood by those of skill in the art that stringency conditions may be increased by increasing temperature, such as to about 60° C. or decreasing salt, such as to about 1×SSC, or may be decreased by increasing salt, for example to about 10×SSC, or decreasing temperature, such as to about 25° C.

Nucleic acids provided by the invention include those encoding active ECS1 protein fragments. Those of skill in the art will immediately understand that polypeptide fragments may be prepared by placing segments of ECS1 coding sequences in frame in an appropriate expression vector, for example, comprising a plant promoter. Using the methods described in the working examples, the ability of a given polypeptide sequence to confer a phenotypic trait, such as modulation of seed production, can be efficiently confirmed for any given sequence. Fragments of nucleic acids may be prepared according to any of the well known techniques, including partial or complete restriction digests and manual shearing.

Sequences provided by the invention may be defined as encoding a functional (e.g., active) ECS1 protein. In certain further aspects of the invention, a plant ECS1 protein may be characterized as from a monocotyledonous or dicotyledonous plant. Coding sequences may be provided operably linked to a heterologous promoter, in sense or antisense orientation. Expression constructs are also provided comprising these sequences, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with ECS1 protein coding sequences. The ECS1 protein coding sequence may be provided with other sequences for efficient expression as is known in the art. One or more selectable marker genes may be co-introduced into a plant with a nucleic acid provided by the invention.

The choice of any additional elements used in conjunction with an ECS1 coding sequence will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al., (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of an ECS1 coding sequence is used. In certain embodiments, it may be desired to employ developmentally regulated promoters such that ECS1 gene expression is triggered in concert with seed production for an increase in seed count and/or yield, but wherein expression is limited during other times.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that ECS1 protein coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a ECS1 coding sequence is used. Alternatively, a heterologous 3' end may enhance the expression of ECS1 coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

II. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-mediated Transformation *Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al, 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a coding sequence may be heterologous in that it is linked to a different promoter sequence relative to the native coding sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VI. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Identification of ECS1, a Gene Conferring Increased Seed Production

BRS1 encodes a secreted serine carboxypeptidase that is implicated in an early step in brassinosteroid signaling, and is indicated as taking part in the proteolytic processing of a protein involved in activating the BRI1 receptor (Li et al., 2001). The protease activity of BRS1 is required for its function in suppressing the phenotypes of a weak BRI1 allele, bri1-5. BRS1 is a member of a serine carboxypeptidase gene family in *Arabidopsis*. The fact that a loss-of-function allele of BRS1 does not show any significant phenotypes suggested there is functional redundancy among the family members.

To test if other members of the gene family play similar roles in suppressing the phenotypes of bri1-5, five closely related homologues of BRS1 were chosen and the corresponding cDNAs of these homologues expressed under a 35S promoter in bri1-5 plants by *Agrobacterium*-mediated transformation (Clough and Bent 1998). Results showed that three out of the five BRS1-related genes suppressed the phenotype of the bri1-5 allele. Among these three homologues, ECS1 produced an additional phenotype, i.e., increases in the numbers of carpels and seeds as described in more detail below.

EXAMPLE 2

Overexpression of ECS1

Overexpressing ECS1 under a strong constitutive promoter in wild type *Arabidopsis* plants was demonstrated to increase the numbers of carpels and seeds per silique (FIG. 1). Wild-type *Arabidopsis* plants have two carpels. In contrast, ECS1-overexpressing lines had three carpels, although some siliques had four carpels. Wild type plants have an average seed number of 66.2 seed/silique, whereas ECS1-overexpressing lines had 88.1 seeds per silique. The weight of 1000 seeds from ECS1-overexpressing plants was not significantly different from that of wildtype, showing that these seeds are of normal size and shape. However, the total seed weight/silique was increased by about 33% in ECS1-overexpressing plants due to the increased total number of seeds.

As can be seen in FIG. 1, wildtype plants had a low level of ECS1, while the ECS1-overexpressing line (in WS background) had an elevated ECS1 expression level (top panel). ACT7 was used as a probe to show the sample equal loading of total RNA (bottom panel).

Figure 3:
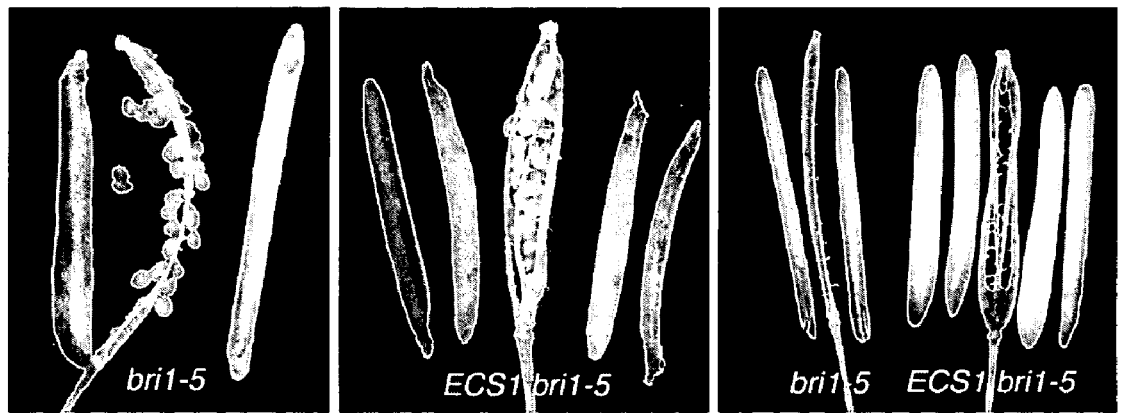
FIG. 3. Siliques of bri1-5 and ECS1 bri1-5. The left and center panels show the dissected green siliques with seeds attached. The right panel compares the siliques of bri1-5 and ECS1 bri1-5 after removal of the seeds. Four carpels in ECS1 bri1-5 contrast two carpels in bri1-5.

The overexpression of ECS1 suppressed the bri1-5 phenotype. Rossette leaves in bri1-5 are curled, while ECS1-overexpressing plants have expanded leaves. bri1-5 plants flower 7-10 days later than wildtype plants, while ECS1-overexpressing plants flower 5-7 days earlier than bri1-5 plant. Interestingly, ECS1-overexpressing lines in bri1-5 had four-carpel siliques (FIG. 3). Carpels are the ovule (seed)-bearing organ in gynoecium, and the increased carpel numbers lead to elevated seed numbers per silique. A two-carpel silique from bri1-5 plants has an average of 43.2 seeds, while the four-carpel silique from ECS1-overexpressing plants increased the seed number to 58.3 seeds/silique.

Data was collected regarding seed yield in a population of ECS1-overexpressing transgenic plants (35S::ECS1; 28 plants) and a population of wild-type plants (29 plants) grown to maturity in the greenhouse. Total seed was collected from each individual and weighed to determine total seed yield per plant (Table 1).

TABLE 1 analysis of total seed yield.

|  | 35S::ECS1 | Wild-type |
| --- | --- | --- |
| Mean seed weight/plant (gm) | .82 | .77 |
| SD (gm) | .16 | .13 |
| N | 28 | 29 |

P value = .178

Statistical analysis of the data indicated that the seed yield from the two populations was not statistically different. Because the 35S::ECS1 plants produce more seed per fruit, this result suggests that the ECS1-overexpressing plants have fewer fruit per plant. This would be consistent with qualitative observations that the 35S::ECS1 plants used in this study were somewhat smaller than wildtype and appeared to produce fewer flowers.

There were several possible explanations for why an increase in total seed yield per plant was not observed. The 35S::ECS1 transgenic lines used in this study were all siblings and the result may be due to a transgene position effect. Several independent 35S::ECS1 lines were analyzed in the bri1-5 background and the increased carpel number and seed per fruit was consistent. In addition, there were likely background differences between the 35S::ECS1 transgenic lines and the wild type. The 35S::ECS1 transgenic line is the result of crossing 35S::ECS1 bri1-5 with wild type and isolating plants that were wildtype for BRI1. To control for these variables, additional, independent 35S::ECS1 lines are being generated in the Col ecotype for comparison of total seed yield between these lines and the Col wildtype. The use of tissues specific promoters to limit ECS1 expression in flowers and fruits will also be analyzed.

EXAMPLE 3

Identification of Orthologous Plant Coding Sequences

Database searching was carried out to reveal ECS1 sequences in *Arabidopsis,* rice, barley, pea, Medicago. The sequence database accession numbers of ECS1 and some of its homologs and orthologs identified are listed in Table 1. The five most closely related *Arabidopsis* sequences are aligned with ECS1 in FIG. 4. Amino acids that match ECS1 are shaded in black. ECS1 is 72% identical to BRS1 at the amino acid sequence level. The homologies between ECS1 and homologs 2-4 range from 52% to 60%. The homologies in the middle part of these proteins are lower than those of N-terminal and C-terminal parts. It is worth noting that homolog 1 shares 75% identity to ECS1 but lacks a N-terminal signal peptide. Interestingly, overexpression of *Arabidopsis* ECS1 homologue 1 does not suppress the bri1-5 defects and does not have the ECS1 silique phenotype.

TABLE 2

Sequence Database Accession Numbers of *Arabidopsis* ECS1 and its Homologues and Orthologs

| Name | Accession Number | SEQ ID NO |
| --- | --- | --- |
| *Arabidopsis* ECS1 | AAC63668.1 | SEQ ID NOs: 1-2 |
| *Arabidopsis* ECS1 homolog 1 | AAC63669.1 | SEQ ID NO: 16 |
| *Arabidopsis* ECS1 homolog 2 | AAO11573.1 and AAM65698.1 | SEQ ID NO: 17 |
| *Arabidopsis* ECS1 homolog 3 | AAM65590.1 | SEQ ID NO: 18 |
| *Arabidopsis* ECS1 homolog 4 | AAF21209.1 | SEQ ID NO: 19 |
| Rice ECS1 | AK111818; BAD19260 | SEQ ID NOs: 3-4 |
| Rice ECS1 homolog 1 | NM_190464; NP_915353 | SEQ ID NOs: 4-5 |
| Rice ECS1 homolog 2 | NM_184451; NP_909340 | SEQ ID NOs: 24-25 |
| Rice ECS1 homolog 3 | AK111801; BAD19262 | SEQ ID NOs: 26-27 |
| Rice ECS1 homolog 4 | AP004069; BAD25094 | SEQ ID NOs: 28-29 |
| Rice ECS1 homolog 5 | NM_197584; NP_922566 | SEQ ID NOs: 30-31 |
| Rice ECS1 homolog 6 | AC051633; AAG13597 | SEQ ID NOs: 32-33 |
| Barley ECS1 | Y09602; P08818, T05701 | SEQ ID NOs: 7-8 |
| Barley homolog 1 | X78878; P55748 | SEQ ID NOs: 9-10 |
| Wheat ECS1 | A29639 | SEQ ID NO: 11 |
| Pea ECS1 | AJ251969; CAC19488 | SEQ ID NOs: 12-13 |
| *Medicago* ECS1 | AY308957; AAQ63884 | SEQ ID NOs: 14-15 |

The homology between ECS1, BRS1 and other type II serine carboxypeptidases indicated that ECS1 is a serine carboxypeptidase II-like protein. In addition, like BRS1, ECS1 is predicted to have an N terminal signal peptide and should be secreted.

Figure 5:
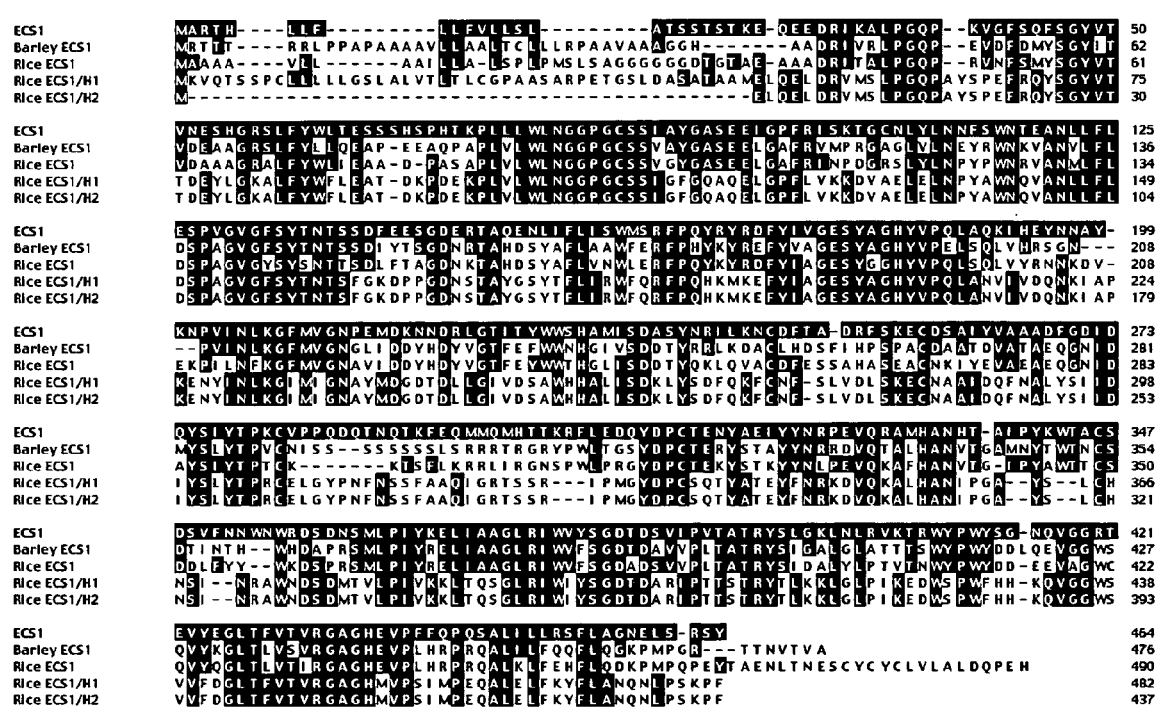

As the rice genomic sequence is available, at least 5 ECS1 orthologs were first identified in rice. The alignment of the predicted amino acid sequence of ECS1 with those of the three most related rice orthologs, as well as d barley ortholog, is shown in FIG. 5.

Similar to the fact that *Arabidopsis* ECS1 has a high sequence identity compared to homologue 1 in *Arabidopsis*, but homologue 1 lacks an N-terminal signal peptide, the two rice orthologs (i.e., rice ECS1/H1 and rice ECS/H2) are identical to each other except that that rice ECS1/H2 lacks the N-terminal signal peptide as seen in rice ECS1/H1.

EXAMPLE 4

Expression of ECS1 and Orthologous Sequences in Selected Crop Species

The ECS1 family of genes is conserved in plants and therefore it can be predicted that overexpression of ECS1 may be used in multiple crop species to increase yield and productivity. A plan was initiated for introduction of the *Arabidopsis* ECS1 gene and identified orthologous sequences into selected crop plants including soybean, canola, maize, barley and rice. Essentially the same gene construct described above is used, consisting of a two-enhancer 35S promoter driving the ECS1 cDNA from *Arabidopsis*. Following initial expression, further studies are carried out for optimization of expression in plants grown under field conditions.

*Brassica napus* (Canola/rape) is a major oil crop closely related to *Arabidopsis. Agrobacterium*-mediated transformation of *Brassica* has been proven to be a routinely successful approach in recent years and therefore is the selected transformation method (Chakrabarty et al., 2002; Stewart et al., 2002). Soybeans will be transformed using the protocols described by Liu et al. (2004) and Zeng et al. (2004). Rice will be transformed with the ECS1-overexpressing construct using well known techniques (see, e.g., Lin et al., 2003; Garg et al., 2002; Wu et al., 2002; Khanna and Raina, 2002). The additional monocotyledonous species maize and barley will also be transformed using known methods for generating transgenic plants (see, e.g., Zhong et al., 1996; Horvath et al., 2003; Wan and Lemaux, 1994; Roussy et al., 2001).

Initially 10-15 transgenic plants will be obtained for each transgene (ECS1 overexpression and controls) for canola, soybean, rice and other seed crop plants. The phenotypes of the resulting T1 transgenic plants will be measured, including carpel and seed numbers, and the vegetative parts of the plants analyzed for any obvious phenotypic changes. Upon confirmation of seed yield for a given construct in the T1 ECS1 overexpressing plants, Mendelian inheritance of the phenotype will be confirmed in the T2 generation.

Following initial studies with the *Arabidopsis* ECS1 gene, optimization studies are carried out with ECS1 orthologs from other species. The rice (SEQ ID NOs:3 and 5), barley (SEQ ID NOs:7 and 9), wheat (SEQ ID NO:11), pea (SEQ ID NO:12) and Medicago (SEQ ID NO:14) ECS1 orthologous coding sequences are introduced. Sequences are selected for introduction into related species, such as among rice, barley and wheat.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042

Abdullah et al., *Biotechnology*, 4:1087, 1986.
Barr, *Cell*, 66:1-3, 1991.
Bates, *Mol. Biotechnol.*, 2(2):135-145, 1994.
Battraw and Hall, *Theor. App. Genet.*, 82(2):161-168, 1991.
Berger and Altmann, *Genes Dev.*, 14:1119-1131, 2000.
Bevan et al., *Nucleic Acids Research*, 11(2):369-385, 1983.
Bhattacharjee et al., *J. Plant Bioch. and Biotech.* 6, (2):69-73. 1997.
Bower et al., *Plant Journal*, 2:409-416. 1992.
Buising and Benbow, *Mol Gen Genet*, 243(1):71-81. 1994.
Callis et al., *Genes Dev.*, 1:1183-1200, 1987.
Casa et al., *Proc. Natl. Acad. Sci. USA*, 90(23):11212-11216, 1993.
Chakrabarty et al., *J. Biosci.*, 27:495-502, 2002.
Chandler et al., *The Plant Cell*, 1:1175-1183, 1989.
Christou; et al., *Proc. Natl. Acad. Sci. USA*, 84(12):3962-3966, 1987.
Chu et al., *Scientia Sinica*, 18:659-668, 1975.
Clough and Bent, *Plant J.*, 16:735-743, 1998.
Conkling et al., *Plant Physiol.*, 93:1203-1211, 1990.
DE App. 3642,829
De Block et al., *EMBO Journal*, 6(9):2513-2518, 1987.
De Block et al., *Plant Physiol.*, 91:694-701, 1989.
Dellaporta et al., In: *Chromosome Structure and Function: Impact of New Concepts, 18th Stadler Genetics Symposium*, 11:263-282, 1988.
D'Halluin et al., *Plant Cell*, 4(12):1495-1505, 1992.
Dmochowska et al., *Cell*, 50:573-584, 1987.
Ebert et al., 84:5745-5749, *Proc. Natl. Acad. Sci. USA*, 1987.
EPA 154,204
Fraley et al., *Bio/Technology*, 3:629-635, 1985.
Fricker and Leiter, *Trends Biochem. Sci.*, 24:390-393, 1999.
Friedrichsen et al., *Plant Physiol.*, 123:1247-1256, 2000.
Fromm et al., *Nature*, 319:791-793, 1986.
Fuller et al., *Science*, 246:482-486, 1989.
Gallie et al., *The Plant Cell*, 1:301-311, 1989.
Garg et al., *Proc. Natl. Acad. Sci. USA*, 99:15898-903, 2002.
Gelvin et al., In: *Plant Molecular Biology Manual*, 1990.
Ghosh-Biswas et al., *J. Biotechnol.*, 32(1): 1-10, 1994.
Hagio et al., *Plant Cell Rep.*, 10(5):260-264, 1991.
Hamilton et al., *Proc. Natl. Acad. Sci. USA*, 93(18):9975-9979, 1996.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35(1-2):205-218, 1997.
Hinchee et al., *Bio/technol.*, 6:915-922, 1988.
Horvath et al., *Proc. Natl. Acad. Sci. USA*, 100:364-9, 2003.
Hou and Lin, *Plant Physiology*, 111:166, 1996.
Hudspeth and Grula, *Plant Mol. Biol.*, 12:579-589, 1989.
Ikuta et al., *Bio/technol.*, 8:241-242, 1990.
Ishidia et al., *Nat. Biotechnol.*, 14(6):745-750, 1996.
Kaeppler et al., *Plant Cell Reports* 9: 415-418, 1990.
Kaeppler et al., *Theor. Appl. Genet.*, 84(5-6):560-566, 1992.
Katz et al., *J. Gen. Microbiol.*, 129:2703-2714, 1983.
Khanna and Raina, *Transgenic Res.*, 11:411-23, 2002.
Klee et al., *Bio-Technology*, 3(7):637-642, 1985.
Knittel et al., *Plant Cell Reports*, 14(2-3):81-86, 1994.
Lawton et al., *Plant Mol. Biol.* 9:315-324, 1987.
Lazzeri, *Methods Mol. Biol.*, 49:95-106, 1995.
Lee et al., *Korean J. Genet.*, 11(2):65-72, 1989.
Li et al., *Proc. Natl. Acad. Sci. USA*, 98:5916-5921, 2001.
Lin et al., *Proc. Natl. Acad. Sci. USA*, 100:5962-7, 2003.
Liu Planta., 2004 [Epub ahead of print].
Lorz et al., *Mol Gen Genet*, 199:178-182, 1985.
McCabe, Martinell, *Bio-Technology*, 11(5):596-598, 1993.
McCormac et al., *Euphytica*, 99(1):17-25, 1998.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11(7):471-473, 1997.
Naggert et al., *Nat. Genet.*, 10:135-142, 1995.
Neuteboom et al., *Plant Mol. Biol.*, 39:273-287, 1999.
Odell et al., *Nature*, 313:810-812, 1985.
Ogawa et al., *Sci. Rep.*, 13:42-48, 1973.
Omirulleh et al., *Plant Mol. Biol.*, 21(3):415-428, 1993.
Ow et al., *Science*, 234:856-859, 1986.
PCT App. WO 92/17598
PCT App. WO 94/09699
PCT App. WO 95/06128
PCT App. WO 97/4103
PCT App. WO 97/41228
Potrykus et al., *Mol. Gen. Genet.*, 199:183-188, 1985.
Prasher et al., *Biochem. Biophys. Res. Commun.*, 126(3): 1259-1268, 1985.
Reichel et al., *Proc. Natl. Acad. Sci. USA*, 93 (12) p. 5888-5893. 1996.
Rhodes et al., *Methods Mol. Biol.*, 55:121-131, 1995.
Ritala et al., *Plant Mol. Biol.*, 24(2):317-325, 1994.
Rogers et al., *Methods Enzymol.*, 153:253-277, 1987.
Roussy et al., *Hereditas*, 134:97-101, 2001.
Sambrook et al., In: *Molecular Cloning-A Laboratory Manual* (second edition), Cold Spring Harbour Laboratory Press, 1989.
Schaller and Ryan, *Proc. Natl. Acad. Sci. USA*, 91:11802-11806, 1994.
Sheen et al., *Plant Journal*, 8(5):777-784, 1995.
Singsit et al., *Transgenic Res.*, 6(2):169-176, 1997.
Spencer et al., *Plant Mol. Biol.*, 18(2):201-210, 1992.
Stalker et al., *Science*, 242:419-422, 1988.
Stewart et al., *Methods Mol. Biol.*, 183:245-252, 2002.
Sullivan et al., *Mol. Gen. Genet.*, 215(3):431-440, 1989.
Sutcliffe, *Proc. Natl. Acad. Sci. USA*, 75:3737-3741, 1978.
Thillet et al., *J. Biol. Chem.*, 263:12500-12508, 1988.
Thomas et al., *Plant Sci.* 69:189-198, 1990.
Thompson et al., *Euphytica*, 85(1-3):75-80, 1995.
Thompson et al., *The EMBO Journal*, 6(9):2519-2523, 1987.
Tian, Sequin, Charest, *Plant Cell Rep.*, 16:267-271, 1997.
Tingay et al., *The Plant Journal* v. 11 (6) p. 1369-1376. 1997.
Tomes et al., *Plant. Mol. Biol.* 14(2):261-268, 1990.
Torbet, Rines, Somers, *Crop Science*, 38(1):226-231, 1998.
Torbet, Rines, Somers, *Plant Cell Reports*, 14(10):635-640, 1995.
Toriyama et al., *Theor Appl. Genet.*, 73:16, 1986.
Tomero et al., *Plant J.*, 10:315-330, 1996.
Tsukada; Kusano; Kitagawa, *Plant Cell Physiol.*, 30(4)599-604, 1989.
Twell et al., *Plant Physiol* 91:1270-1274, 1989.
Uchimiya et al., *Mol. Gen. Genet.*, 204:204, 1986.
Van Eck; Blowers; Earle, *Plant Cell Reports*, 14(5):299-304, 1995.
Vasil et al., *Plant Physiol.*, 91:1575-1579, 1989.
Walker et al., *Proc. Natl. Acad. Sci. USA*, 84:6624-6628, 1987.
Wan and Lemaux, *Plant Physiol.*, 104:37-48, 1994.
Wang et al., *Molecular and Cellular Biology*, 12(8):3399-3406, 1992.
Wu et al., *Transgenic Res.*, 11:553-541, 2002.
Yamada et al., *Plant Cell Rep.*, 4:85, 1986.
Yang and Russell, *Proc. Natl. Acad. Sci. USA*, 87:4144-4148, 1990.
Zeng et al., *Plant Cell Rep.*, 22(7):478-482, 2004.
Zheng and Edwards, *J. Gen. Virol.*, 71:1865-1868, 1990.
Zhong et al., *Plant Physiol.*, 110:1097-107, 1996.
Zhou et al., *Plant Cell Reports*, 12(11).612-616, 1993.
Zukowsky et al., *Proc. Natl. Acad. Sci. USA*, 80:1101-1105, 1983.

What is claimed is:

1. A transgenic plant transformed with a transformation construct comprising the isloated nucleic acid sequence of SEQ ID NO: 1 operably linked with a heterologous promoter functional in plant cells, wherein the plant has increased seed production and/or yield.

2. The transgenic plant of claim 1, further defined as an $R_0$ transgenic plant.

3. A transgenic seed of the transgenic plant of claim 1.

4. A transgenic cell of the transgenic plant of claim 1.

5. A method for increasing seed production and/or yield in a plant comprising introducing into the plant a transformation construct comprising an isolated nucleic acid sequence encoding SEQ ID NO:2, said nucleic acid sequence is operably linked to a heterologous promoter.

6. The method of claim 5, wherein the number of seed produced by the transgenic plant is increased relative to a plant of the same genotype lacking the isolated nucleic acid sequence.

7. The method of claim 5, wherein the weight of seed produced by the transgenic plant is increased relative to a plant of the same genotype lacking the isolated nucleic acid sequence.

8. The method of claim 5, wherein introducing the isolated nucleic acid comprises plant breeding.

9. The method of claim 5, wherein introducing the isolated nucleic acid comprises genetic transformation.

10. A method of preparing seed comprising:
    (a) allowing the transgenic plant of claim 1 to produce seed; and
    (b) collecting seed produced by the plant.

11. The method of claim 5, wherein the heterologous promoter is a developmentally-regulated, organelle-specific, inducible, tissue-specific, constitutive, cell-specific, seed specific, or germination-specific promoter.

* * * * *

UNITED STATES PATENT AND TRADEMARK OFFICE
CERTIFICATE OF CORRECTION

PATENT NO. : 7,601,886 B2
APPLICATION NO. : 11/198886
DATED : October 13, 2009
INVENTOR(S) : John C. Walker et al.

It is certified that error appears in the above-identified patent and that said Letters Patent is hereby corrected as shown below:

In claim 1, column 91, line 47, delete "isloated" and insert --isolated-- therefor.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,886 B2 | Page 1 of 1 |
| APPLICATION NO. | : 11/198886 | |
| DATED | : October 13, 2009 | |
| INVENTOR(S) | : Walker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 212 days.

Signed and Sealed this

Fifth Day of October, 2010

David J. Kappos
*Director of the United States Patent and Trademark Office*

SEQUENCE LISTING

<160> NUMBER OF SEQ ID NOS: 33

<210> SEQ ID NO 1
<211> LENGTH: 1395
<212> TYPE: DNA
<213> ORGANISM: Arabidopsis thaliana

<400> SEQUENCE: 1

| | | | | | |
|---|---|---|---|---|---|
| atggcaagaa | cccacttact | ctttcttcta | tttgtgctct | tatcattagc | aacatcatca | 60 |
| acatcaacaa | aagagcaaga | ggaggacagg | atcaaagcac | taccagggca | accaaaagta | 120 |
| ggattctcac | aattttcggg | ttacgtgaca | gtgaacgagt | cacatggccg | atcactcttc | 180 |
| tactggctca | ccgagtcatc | ttctcattct | cctcacacca | aaccacttct | tctttggctc | 240 |
| aatggaggac | caggctgctc | gtcgattgct | tatggagctt | cggaggaaat | tggaccattt | 300 |
| cggatcagca | aaaccggttg | caatctttat | ctcaacaact | tttcttggaa | cagagggca | 360 |
| aaccttttat | ttcttgaatc | gcctgttggt | gttggatttt | catatactaa | cacaagctcg | 420 |
| gattttgaag | aatccggaga | cgaacgtaca | gctcaggaaa | atttgatatt | tcttataagt | 480 |
| tggatgtcaa | gatttcctca | gtaccggtat | agagatttct | acattgttgg | tgaaagctac | 540 |
| gccggtcatt | atgttcctca | gctcgcccaa | aaaattcatg | agtacaacaa | cgcctacaaa | 600 |
| aatccagtaa | tcaatcttaa | aggtttcatg | gttggtaacc | cagagatgga | caaaacaac | 660 |
| gacagactag | ggacgataac | gtattggtgg | tctcacgcga | tgatctcgga | cgcttcctac | 720 |
| aatcgcatcc | tcaaaaactg | tgattttaca | gcggatagat | tctccaaaga | atgcgattcc | 780 |
| gccatttatg | tcgctgctgc | cgactttggc | gacatcgatc | agtacagcat | ctacacaccc | 840 |
| aagtgtgtac | caccacaaga | ccaaacgaac | cagaccaagt | ttgagcagat | gatgcaaatg | 900 |
| cacacaacta | aaaggttttt | agaagatcag | tatgacccct | tgtaccgaaaa | ctatgccgag | 960 |
| atatattata | accgtcctga | ggtacaacga | gctatgcatg | ctaaccacac | tgccattcca | 1020 |
| tataagtgga | ctgcttgcag | tgactctgtc | tttaataact | ggaattggag | agattccgac | 1080 |
| aattcaatgt | taccgatata | taggaactc | attgctgctg | gtctaagaat | ctgggtctac | 1140 |
| agtggtgata | cagattcggt | aattccagtg | acagcgactc | gatattccct | tggcaaactg | 1200 |
| aatcttcgag | tgaaaactcg | ctggtaccct | tggtactccg | gaaaccaggt | aggaggacga | 1260 |
| acagaagtat | acgaggggct | tacctttgtg | acggtaagag | gggcgggca | cgaggtgcca | 1320 |
| ttcttccaac | cgcaaagtgc | gcttattctt | ttaagatcat | tcttggctgg | aaatgagctt | 1380 |
| tcaagatctt | attag | | | | | 1395 |

<210> SEQ ID NO 2
<211> LENGTH: 464
<212> TYPE: PRT
<213> ORGANISM: Arabidopsis thaliana

<400> SEQUENCE: 2

Met Ala Arg Thr His Leu Leu Phe Leu Leu Phe Val Leu Leu Ser Leu
 1               5                  10                  15

Ala Thr Ser Ser Thr Ser Thr Lys Glu Gln Glu Glu Asp Arg Ile Lys
            20                  25                  30

Ala Leu Pro Gly Gln Pro Lys Val Gly Phe Ser Gln Phe Ser Gly Tyr
        35                  40                  45

Val Thr Val Asn Glu Ser His Gly Arg Ser Leu Phe Tyr Trp Leu Thr
    50                  55                  60

```
Glu Ser Ser Ser His Ser Pro His Thr Lys Pro Leu Leu Leu Trp Leu
 65                  70                  75                  80

Asn Gly Gly Pro Gly Cys Ser Ser Ile Ala Tyr Gly Ala Ser Glu Glu
                 85                  90                  95

Ile Gly Pro Phe Arg Ile Ser Lys Thr Gly Cys Asn Leu Tyr Leu Asn
            100                 105                 110

Asn Phe Ser Trp Asn Thr Glu Ala Asn Leu Leu Phe Leu Glu Ser Pro
        115                 120                 125

Val Gly Val Gly Phe Ser Tyr Thr Asn Thr Ser Ser Asp Phe Glu Glu
    130                 135                 140

Ser Gly Asp Glu Arg Thr Ala Gln Glu Asn Leu Ile Phe Leu Ile Ser
145                 150                 155                 160

Trp Met Ser Arg Phe Pro Gln Tyr Arg Tyr Arg Asp Phe Tyr Ile Val
                165                 170                 175

Gly Glu Ser Tyr Ala Gly His Tyr Val Pro Gln Leu Ala Gln Lys Ile
            180                 185                 190

His Glu Tyr Asn Asn Ala Tyr Lys Asn Pro Val Ile Asn Leu Lys Gly
        195                 200                 205

Phe Met Val Gly Asn Pro Glu Met Asp Lys Asn Asn Asp Arg Leu Gly
    210                 215                 220

Thr Ile Thr Tyr Trp Trp Ser His Ala Met Ile Ser Asp Ala Ser Tyr
225                 230                 235                 240

Asn Arg Ile Leu Lys Asn Cys Asp Phe Thr Ala Asp Arg Phe Ser Lys
                245                 250                 255

Glu Cys Asp Ser Ala Ile Tyr Val Ala Ala Ala Asp Phe Gly Asp Ile
            260                 265                 270

Asp Gln Tyr Ser Ile Tyr Thr Pro Lys Cys Val Pro Pro Gln Asp Gln
        275                 280                 285

Thr Asn Gln Thr Lys Phe Glu Gln Met Met Gln Met His Thr Thr Lys
    290                 295                 300

Arg Phe Leu Glu Asp Gln Tyr Asp Pro Cys Thr Glu Asn Tyr Ala Glu
305                 310                 315                 320

Ile Tyr Tyr Asn Arg Pro Glu Val Gln Arg Ala Met His Ala Asn His
                325                 330                 335

Thr Ala Ile Pro Tyr Lys Trp Thr Ala Cys Ser Asp Ser Val Phe Asn
            340                 345                 350

Asn Trp Asn Trp Arg Asp Ser Asp Asn Ser Met Leu Pro Ile Tyr Lys
        355                 360                 365

Glu Leu Ile Ala Ala Gly Leu Arg Ile Trp Val Tyr Ser Gly Asp Thr
    370                 375                 380

Asp Ser Val Ile Pro Val Thr Ala Thr Arg Tyr Ser Leu Gly Lys Leu
385                 390                 395                 400

Asn Leu Arg Val Lys Thr Arg Trp Tyr Pro Trp Tyr Ser Gly Asn Gln
                405                 410                 415

Val Gly Gly Arg Thr Glu Val Tyr Glu Gly Leu Thr Phe Val Thr Val
            420                 425                 430

Arg Gly Ala Gly His Glu Val Pro Phe Phe Gln Pro Gln Ser Ala Leu
        435                 440                 445

Ile Leu Leu Arg Ser Phe Leu Ala Gly Asn Glu Leu Ser Arg Ser Tyr
    450                 455                 460

<210> SEQ ID NO 3
<211> LENGTH: 1422
```

```
<212> TYPE: DNA
<213> ORGANISM: Oryza sativa

<400> SEQUENCE: 3
atggcgacgc gagggcggat tgtagcggcg gtggcgagcg ttgtggtggc gtggctggcg      60
gtcgccgtcg gcgtgaacgg cggcgggtgc gaggcggagc gggaccgggt ggaggcgctg     120
ccggggcagc accggtggc gttcgcgcag tacgccgggt acgtggcggt gagcgaggcg      180
agcgggcggg cgctcttcta ctggctcacc gaggccgccg ccgccgccgc cgccgccacc     240
aagcccctcg tcctctggct caacggcggt cctggatgct catcgattgc gtatggagca     300
tctgaagaga ttggcccatt taggattaag acaaacggga cagggctcta tctgaacaag     360
tactcatgga cagagaggc aaacctcctg ttcctggaat cacctgccgg agttggcttt      420
tcatactcca acaccacctc tgatctcaag acatctggtg atgagaggac agctcaagat     480
gcgttgcagt tcttgatcag ttggatgtcc cgcttccac agtatcggca ccgggatttc      540
tacattgctg agaaagcta tgctggacat tacgttcccc agttggcaag gaagatcgtt     600
gagttcaaca aggcctcacc atatcctttc atcaacctca aggggatcct tgtgggcaat     660
ggggtgactg acaactacta cgacaacatc ggcacggtga cctactggtg gacgcacgcc     720
atgatctcgg acaccaccta caaggccatc atgtcgtcgt gcaacttcac cagcgccaac     780
gtctccaggc tctgcaaccg cgccatgagc tacgccatga ccacgagtt cggcgacatc      840
gaccagtaca gcatctacac gccgtcctgc gccgccgccg ccgccgccaa cgccaccggc     900
cgccgccgcg gcaaggccgc cgtgctgagg ttcaaggaca ccttcctacg cgccggtcg      960
ttcggctacg accctgcac ggagacatac gccgagaagt actacaaccg gccggatgtt     1020
cagaaggcca tgcatgccaa catcactggg attccttaca gatggacagc ctgcagtgat     1080
gtgctcatca agacgtggcg agattcagag ttctccatgc tgccgactta caagttgctg     1140
atgaaggccg gctgaggat atgggtgttc agtggcgaca cggattcagt cgttccggtt     1200
actgcaacga ggtttgcgct tagccatctt ggactgaaga cgaagatccg ctggtaccct     1260
tggtactcag ctggacaggt tggaggatgg tctgaggtgt atgaagggct cacatttgcg     1320
tcagtgagag gtgctgggca tgaggtgcca ctgtttcagc caaggagagc attcaggatg     1380
tttcagtcgt tcttggcagg ggagccattg ccaaaatcct ga                       1422

<210> SEQ ID NO 4
<211> LENGTH: 473
<212> TYPE: PRT
<213> ORGANISM: Oryza sativa

<400> SEQUENCE: 4

Met Ala Thr Arg Gly Arg Ile Val Ala Ala Val Ala Ser Val Val Val
 1               5                  10                  15

Ala Trp Leu Ala Val Ala Val Gly Val Asn Gly Gly Gly Cys Glu Ala
             20                  25                  30

Glu Arg Asp Arg Val Glu Ala Leu Pro Gly Gln Pro Val Ala Phe
         35                  40                  45

Ala Gln Tyr Ala Gly Tyr Val Ala Val Ser Glu Ala Ser Gly Arg Ala
     50                  55                  60

Leu Phe Tyr Trp Leu Thr Glu Ala Ala Ala Ala Ala Ala Ala Ala Thr
 65                  70                  75                  80

Lys Pro Leu Val Leu Trp Leu Asn Gly Gly Pro Gly Cys Ser Ser Ile
                 85                  90                  95
```

-continued

```
Ala Tyr Gly Ala Ser Glu Glu Ile Gly Pro Phe Arg Ile Lys Thr Asn
                100                 105                 110
Gly Thr Gly Leu Tyr Leu Asn Lys Tyr Ser Trp Asn Arg Glu Ala Asn
            115                 120                 125
Leu Leu Phe Leu Glu Ser Pro Ala Gly Val Gly Phe Ser Tyr Ser Asn
        130                 135                 140
Thr Thr Ser Asp Leu Lys Thr Ser Gly Asp Glu Arg Thr Ala Gln Asp
145                 150                 155                 160
Ala Leu Gln Phe Leu Ile Ser Trp Met Ser Arg Phe Pro Gln Tyr Arg
                165                 170                 175
His Arg Asp Phe Tyr Ile Ala Gly Glu Ser Tyr Ala Gly His Tyr Val
            180                 185                 190
Pro Gln Leu Ala Arg Lys Ile Val Glu Phe Asn Lys Ala Ser Pro Tyr
        195                 200                 205
Pro Phe Ile Asn Leu Lys Gly Ile Leu Val Gly Asn Gly Val Thr Asp
    210                 215                 220
Asn Tyr Tyr Asp Asn Ile Gly Thr Val Thr Tyr Trp Trp Thr His Ala
225                 230                 235                 240
Met Ile Ser Asp Thr Thr Tyr Lys Ala Ile Met Ser Ser Cys Asn Phe
                245                 250                 255
Thr Ser Ala Asn Val Ser Arg Leu Cys Asn Arg Ala Met Ser Tyr Ala
            260                 265                 270
Met Asn His Glu Phe Gly Asp Ile Asp Gln Tyr Ser Ile Tyr Thr Pro
        275                 280                 285
Ser Cys Ala Ala Ala Ala Ala Asn Ala Thr Gly Arg Arg Gly
    290                 295                 300
Lys Ala Ala Val Leu Arg Phe Lys Asp Thr Phe Leu Arg Arg Ser
305                 310                 315                 320
Phe Gly Tyr Asp Pro Cys Thr Glu Thr Tyr Ala Glu Lys Tyr Asn
                325                 330                 335
Arg Pro Asp Val Gln Lys Ala Met His Ala Asn Ile Thr Gly Ile Pro
            340                 345                 350
Tyr Arg Trp Thr Ala Cys Ser Asp Val Leu Ile Lys Thr Trp Arg Asp
        355                 360                 365
Ser Glu Phe Ser Met Leu Pro Thr Tyr Lys Leu Leu Met Lys Ala Gly
    370                 375                 380
Leu Arg Ile Trp Val Phe Ser Gly Asp Thr Asp Ser Val Val Pro Val
385                 390                 395                 400
Thr Ala Thr Arg Phe Ala Leu Ser His Leu Gly Leu Lys Thr Lys Ile
                405                 410                 415
Arg Trp Tyr Pro Trp Tyr Ser Ala Gly Gln Val Gly Gly Trp Ser Glu
            420                 425                 430
Val Tyr Glu Gly Leu Thr Phe Ala Ser Val Arg Gly Ala Gly His Glu
        435                 440                 445
Val Pro Leu Phe Gln Pro Arg Arg Ala Phe Arg Met Phe Gln Ser Phe
    450                 455                 460
Leu Ala Gly Glu Pro Leu Pro Lys Ser
465                 470

<210> SEQ ID NO 5
<211> LENGTH: 2010
<212> TYPE: DNA
<213> ORGANISM: Oryza sativa

<400> SEQUENCE: 5
```

```
atggccatca gtagcagagc agctgcgtgc ggcgcgctca tcttcccgac caccgcatcc      60
gccgctccgg tctcccggag cgtctccgtg gaccaaagag tcagccaccg gcggaggaag     120
gcggtggcgg tggcggccgt gccgcacgcc agcagcggcg gcgcgctgct ggagcggccg     180
gccttcgacc agtcccagct cgacacgctt cccgtgacac aagaaggagg ggacaccgga     240
aggatgaggg acaggagggg ctctggaagc ggtgacagct acaaagtttt gctcatagac     300
gacgcccgcc acaccgagaa gcttgtggag aaggccttgc cgcaggtggt gccgtccgtg     360
accgcggagg cggcgcggca gctcttccac gcgtcccggc agaaaggcgc cgcgctcgtc     420
attgtcgccg tgaagcttct tctacctccg tttcacacgc gcgccctcgc tcgccgccag     480
cgccgccgcc accaccacca ccgccactgc cactatacta atgccgagtt gccgacaccc     540
ccacttgccc cgccgcgtcg ctgcgctaca gcgctagagc gagctagcac actagcagtg     600
agccagtgtc ccgtggtccg gccattggag attttggagc tcgtaatggc tcacaaggcc     660
gcggctctgg tgctgctgct agtgtcagtg tcagtggcgg ccgcggcgtc gggcgaccag     720
gagagcgacc ggatccggga gctccccggg cagccggcga aggtgaggtt ctcgcagtac     780
tccggctacg tgacggtcaa ccaggcgcac ggccgcgcgc tcttctactg gctggtggag     840
gcggtgccgg cggccgggcc catcgcgccg ctcgtcctgt ggctcaacgg cgggccgggg     900
tgctcgtcgg tcgggtacgg cgcgtcggag gaggtcggcc cgttccggat caggcccgac     960
gggaagacgc tgtacctgaa cccccaattct tggaacaagg cggcgaattt gctgttcttg    1020
gagtcgccgc ccgcgtggg gttctcgtac tcgaacaaga cgttggatct gtacgtcgca    1080
ggagatgcta agacagcatc ggatgcttat gcatttctgg tgaactggtt ggagagattc    1140
ccacaataca gtacaggga gttctacatt gctggggaga gctatgcagg gcattacgtt    1200
ccccagttag cccagctcat ctatgaacag aacaagggca ttcagaatcc aataattaat    1260
ctcaaaggat tcatggtggg taatgcggtt actgatgact accacgacta tcttggtacc    1320
tttgagtatt ggtggactca tggcctcatc tctgacaaca cttatcacaa cctgaagaag    1380
acatgcttgc ttgagtcctc tgagcaccct ctcctgaat gtctaaagaa cctgaaccta    1440
gccagttcag aagaaggcaa tatcgatcct tacagcctgt atacaaagcc ctgcaataat    1500
acagcctctc tcaaacttgg cttgggagga cgctacccctt ggttatccag agcatatgat    1560
ccctgcacag aaagatactc aagtatttac tacaaccggc agaagtgca gatagcgatg    1620
catgctaaca ccactgggat tcaatattca tggaaaactt gcagcgatat tgtcggatca    1680
tactgggcag attccccgaa atctatgctt cctatctacc aagaattgat tgcagctggt    1740
atcaggatat gggttttcag tggggataca gatgctgtag ttcctgttac tgcaacaagg    1800
tactcaatag atgctcttaa gcttccaact atggtcaatt ggtacccttg gtatgaccac    1860
ggaaaggttg gaggttggag tcaagtgtat aaaggattaa ctctcgtcac tatagcaggc    1920
gcaggccatg aggtaccact acaccggcct cgagaagcac ttatattatt cagacacttc    1980
ttgcagaata cacccatgcc aactcaatag                                      2010
```

<210> SEQ ID NO 6
<211> LENGTH: 669
<212> TYPE: PRT
<213> ORGANISM: Oryza sativa

<400> SEQUENCE: 6

Met Ala Ile Ser Ser Arg Ala Ala Ala Cys Gly Ala Leu Ile Phe Pro
 1               5                  10                  15

```
Thr Thr Ala Ser Ala Ala Pro Val Ser Arg Ser Val Ser Val Asp Gln
            20                  25                  30

Arg Val Ser His Arg Arg Lys Ala Val Ala Val Ala Val Pro
        35                  40                  45

His Ala Ser Ser Gly Gly Ala Leu Leu Glu Arg Pro Ala Phe Asp Gln
        50                  55                  60

Ser Gln Leu Asp Thr Leu Pro Val Thr Gln Glu Gly Gly Asp Thr Gly
 65                  70                  75                  80

Arg Met Arg Asp Arg Arg Gly Ser Gly Ser Gly Asp Ser Tyr Lys Val
                85                  90                  95

Leu Leu Ile Asp Asp Ala Arg His Thr Glu Lys Leu Val Glu Lys Ala
                100                 105                 110

Leu Pro Gln Val Val Pro Ser Val Thr Ala Glu Ala Ala Arg Gln Leu
            115                 120                 125

Phe His Ala Ser Arg Gln Lys Gly Ala Ala Leu Val Ile Val Ala Val
        130                 135                 140

Lys Leu Leu Leu Pro Pro Phe His Thr Arg Ala Leu Ala Arg Arg Gln
145                 150                 155                 160

Arg Arg Arg His His His Arg His Cys His Tyr Thr Asn Ala Glu
                165                 170                 175

Leu Pro Thr Pro Pro Leu Ala Pro Pro Arg Arg Cys Ala Thr Ala Leu
            180                 185                 190

Glu Arg Ala Ser Thr Leu Ala Val Ser Gln Cys Pro Val Val Arg Pro
        195                 200                 205

Leu Glu Ile Leu Glu Leu Val Met Ala His Lys Ala Ala Ala Leu Val
        210                 215                 220

Leu Leu Leu Val Ser Val Ser Val Ala Ala Ala Ala Ser Gly Asp Gln
225                 230                 235                 240

Glu Ser Asp Arg Ile Arg Glu Leu Pro Gly Gln Pro Ala Lys Val Arg
                245                 250                 255

Phe Ser Gln Tyr Ser Gly Tyr Val Thr Val Asn Gln Ala His Gly Arg
            260                 265                 270

Ala Leu Phe Tyr Trp Leu Val Glu Ala Val Pro Ala Ala Gly Pro Ile
        275                 280                 285

Ala Pro Leu Val Leu Trp Leu Asn Gly Gly Pro Gly Cys Ser Ser Val
        290                 295                 300

Gly Tyr Gly Ala Ser Glu Glu Val Gly Pro Phe Arg Ile Arg Pro Asp
305                 310                 315                 320

Gly Lys Thr Leu Tyr Leu Asn Pro Asn Ser Trp Asn Lys Ala Ala Asn
                325                 330                 335

Leu Leu Phe Leu Glu Ser Pro Ala Gly Val Gly Phe Ser Tyr Ser Asn
            340                 345                 350

Lys Thr Leu Asp Leu Tyr Val Ala Gly Asp Ala Lys Thr Ala Ser Asp
        355                 360                 365

Ala Tyr Ala Phe Leu Val Asn Trp Leu Glu Arg Phe Pro Gln Tyr Lys
        370                 375                 380

Tyr Arg Glu Phe Tyr Ile Ala Gly Glu Ser Tyr Ala Gly His Tyr Val
385                 390                 395                 400

Pro Gln Leu Ala Gln Leu Ile Tyr Glu Gln Asn Lys Gly Ile Gln Asn
                405                 410                 415

Pro Ile Ile Asn Leu Lys Gly Phe Met Val Gly Asn Ala Val Thr Asp
            420                 425                 430
```

```
Asp Tyr His Asp Tyr Leu Gly Thr Phe Glu Tyr Trp Trp Thr His Gly
        435                 440                 445

Leu Ile Ser Asp Asn Thr Tyr His Asn Leu Lys Lys Thr Cys Leu Leu
    450                 455                 460

Glu Ser Ser Glu His Pro Ser Pro Glu Cys Leu Lys Asn Leu Asn Leu
465                 470                 475                 480

Ala Ser Ser Glu Glu Gly Asn Ile Asp Pro Tyr Ser Leu Tyr Thr Lys
                485                 490                 495

Pro Cys Asn Asn Thr Ala Ser Leu Lys Leu Gly Leu Gly Gly Arg Tyr
            500                 505                 510

Pro Trp Leu Ser Arg Ala Tyr Asp Pro Cys Thr Glu Arg Tyr Ser Ser
        515                 520                 525

Ile Tyr Tyr Asn Arg Pro Glu Val Gln Ile Ala Met His Ala Asn Thr
    530                 535                 540

Thr Gly Ile Gln Tyr Ser Trp Lys Thr Cys Ser Asp Ile Val Gly Ser
545                 550                 555                 560

Tyr Trp Ala Asp Ser Pro Lys Ser Met Leu Pro Ile Tyr Gln Glu Leu
                565                 570                 575

Ile Ala Ala Gly Ile Arg Ile Trp Val Phe Ser Gly Asp Thr Asp Ala
            580                 585                 590

Val Val Pro Val Thr Ala Thr Arg Tyr Ser Ile Asp Ala Leu Lys Leu
        595                 600                 605

Pro Thr Met Val Asn Trp Tyr Pro Trp Tyr Asp His Gly Lys Val Gly
        610                 615                 620

Gly Trp Ser Gln Val Tyr Lys Gly Leu Thr Leu Val Thr Ile Ala Gly
625                 630                 635                 640

Ala Gly His Glu Val Pro Leu His Arg Pro Arg Glu Ala Leu Ile Leu
                645                 650                 655

Phe Arg His Phe Leu Gln Asn Thr Pro Met Pro Thr Gln
            660                 665

<210> SEQ ID NO 7
<211> LENGTH: 1431
<212> TYPE: DNA
<213> ORGANISM: Hordeum vulgare

<400> SEQUENCE: 7
atgaggacta cgacccgccg tctcccccca gctccggcgg cggcggcggt gctcctggcg    60
gcgttgacgt gcctcctcct ccggccagcc gccgtcgccg cggcgggcgg ccatgccgcg   120
gaccgcatag tccggctgcc ggggcagccg gaggtggact cgacatgta ctccgggtac   180 atcacggtgg acgaggccgc cggacggtcg ctcttctacc tgctgcagga ggcgcccgag   240
gaggcccagc cggcgccgct cgtgctgtgg ctcaacggcg ccccggctg ctcctccgtc    300 gcctacggcg cgtcggagga gctcggcgcg ttccgcgtca tgcccgcgg cgccggcctc    360 gtcctcaacg agtaccgctg gaacaaagtg gccaacgtgc tgttcctgga ttcgccggcc   420
ggcgtggggt tctcctacac caacaccagc tccgacatct acacctccgg cgacaacagg   480
acggcgcacg actcgtacgc cttcctggcg gcatggttcg agaggttccc gcactacaag   540
taccgcgaat tctacgtcgc cggcgagagc tacgccgggc actacgtccc ggagctgtcg   600
cagctggtcc accggagcgg caaccccgtc atcaacctca gggcttcat ggtcggcaac    660 ggcctcatcg acgactacca cgactacgtc ggcaccttcg agttctggtg gaaccacggg   720
atcgtctccg acgacaccta ccgccgcctc aaggacgcct gcctccacga ctccttcatc   780
```

-continued

```
caccccctcgc cggcgtgcga cgccgcgacg gacgtcgcca cggcggagca gggcaacatc      840
gacatgtaca gcctctacac ccccgtctgc aacatctcgt cgtcgtcgtc gtcgtcgtcc      900
ttgagccggc ggcggaccag agggcgctac ccatggctga ccgggtcgta cgacccgtgc      960
acggagaggt actcgacggc gtactacaac cggcgggacg tgcagacggc cctccacgcc     1020
aacgtcaccg cgccatgaa ctacacgtgg gcgacctgca gcgacaccat taatacccac     1080
tggcatgatg ctccgaggtc catgcttccc atctacaggg agctgattgc agctggccta     1140
aggatttggg tcttcagcgg cgacacggat gcggtagtcc ccttgacagc aacaagatac     1200
tccatcggcg ctctgggtct tgcaactact accagttggt acccttggta tgacgacctg     1260
caggaggtcg gcggctggag ccaggtgtac aagggcctta cgctggtgtc cgtcagaggt     1320
gcgggccatg aggttcctct gcaccgtccg cggcaagcgc tcatactgtt tcagcaattc     1380
ctgcagggca agcccatgcc aggccgtacc acaaatgtga cggtggctta a              1431
```

<210> SEQ ID NO 8
<211> LENGTH: 476
<212> TYPE: PRT
<213> ORGANISM: Hordeum vulgare

<400> SEQUENCE: 8

```
Met Arg Thr Thr Thr Arg Arg Leu Pro Pro Ala Pro Ala Ala Ala
  1               5                  10                  15

Val Leu Leu Ala Ala Leu Thr Cys Leu Leu Arg Pro Ala Ala Val
                 20                  25                  30

Ala Ala Ala Gly Gly His Ala Ala Asp Arg Ile Val Arg Leu Pro Gly
             35                  40                  45

Gln Pro Glu Val Asp Phe Asp Met Tyr Ser Gly Tyr Ile Thr Val Asp
     50                  55                  60

Glu Ala Ala Gly Arg Ser Leu Phe Tyr Leu Leu Gln Glu Ala Pro Glu
 65                  70                  75                  80

Glu Ala Gln Pro Ala Pro Leu Val Leu Trp Leu Asn Gly Gly Pro Gly
                 85                  90                  95

Cys Ser Ser Val Ala Tyr Gly Ala Ser Glu Glu Leu Gly Ala Phe Arg
            100                 105                 110

Val Met Pro Arg Gly Ala Gly Leu Val Leu Asn Glu Tyr Arg Trp Asn
        115                 120                 125

Lys Val Ala Asn Val Leu Phe Leu Asp Ser Pro Ala Gly Val Gly Phe
    130                 135                 140

Ser Tyr Thr Asn Thr Ser Ser Asp Ile Tyr Thr Ser Gly Asp Asn Arg
145                 150                 155                 160

Thr Ala His Asp Ser Tyr Ala Phe Leu Ala Ala Trp Phe Glu Arg Phe
                165                 170                 175

Pro His Tyr Lys Tyr Arg Glu Phe Tyr Val Ala Gly Glu Ser Tyr Ala
            180                 185                 190

Gly His Tyr Val Pro Glu Leu Ser Gln Leu Val His Arg Ser Gly Asn
        195                 200                 205

Pro Val Ile Asn Leu Lys Gly Phe Met Val Gly Asn Gly Leu Ile Asp
    210                 215                 220

Asp Tyr His Asp Tyr Val Gly Thr Phe Glu Phe Trp Trp Asn His Gly
225                 230                 235                 240

Ile Val Ser Asp Asp Thr Tyr Arg Arg Leu Lys Asp Ala Cys Leu His
                245                 250                 255

Asp Ser Phe Ile His Pro Ser Pro Ala Cys Asp Ala Ala Thr Asp Val
```

```
                260             265             270
Ala Thr Ala Glu Gln Gly Asn Ile Asp Met Tyr Ser Leu Tyr Thr Pro
            275                     280                 285

Val Cys Asn Ile Ser Ser Ser Ser Ser Ser Ser Leu Ser Arg Arg
        290                     295                 300

Arg Thr Arg Gly Arg Tyr Pro Trp Leu Thr Gly Ser Tyr Asp Pro Cys
305                     310                  315                 320

Thr Glu Arg Tyr Ser Thr Ala Tyr Tyr Asn Arg Arg Asp Val Gln Thr
                    325                 330                 335

Ala Leu His Ala Asn Val Thr Gly Ala Met Asn Tyr Thr Trp Thr Asn
                340                  345                 350

Cys Ser Asp Thr Ile Asn Thr His Trp His Asp Ala Pro Arg Ser Met
            355                 360                 365

Leu Pro Ile Tyr Arg Glu Leu Ile Ala Ala Gly Leu Arg Ile Trp Val
        370                 375                 380

Phe Ser Gly Asp Thr Asp Ala Val Val Pro Leu Thr Ala Thr Arg Tyr
385                 390                 395                 400

Ser Ile Gly Ala Leu Gly Leu Ala Thr Thr Ser Trp Tyr Pro Trp
                    405                 410                 415

Tyr Asp Asp Leu Gln Glu Val Gly Gly Trp Ser Gln Val Tyr Lys Gly
                420                 425                 430

Leu Thr Leu Val Ser Val Arg Gly Ala Gly His Glu Val Pro Leu His
            435                 440                 445

Arg Pro Arg Gln Ala Leu Ile Leu Phe Gln Gln Phe Leu Gln Gly Lys
        450                 455                 460

Pro Met Pro Gly Arg Thr Thr Asn Val Thr Val Ala
465                 470                 475

<210> SEQ ID NO 9
<211> LENGTH: 1580
<212> TYPE: DNA
<213> ORGANISM: Hordeum vulgare

<400> SEQUENCE: 9
cggtgccgcg ggtgccgggg caggccttcg acgccagctt cgcgcactac gccggctacg      60
tcaccgtcag cgaggaccgc ggcgccgcgc tcttctactg gttcttcgag gccgcgcacg     120
acccggcctc caagccgctc ctgctctggc tcaacggagg gcctggttgc tcatcgattg     180
cttttggagt cggggaagaa gtggggcctt ccatgtcaa tgcagacgga aagggcgttc     240
atatgaatcc ttactcttgg aaccaagttg caaatatctt gttccttgat tcaccggttg     300
gtgttggtta ttcatattca aacacctctg ctgattttt aagcaatggg gatgagagga     360
ctgccaagga ttcgttggtg ttcctaacaa gtggcttga cgattccct caatacaagg     420
agcgtgaatt ttatttaact ggagagagct atgctggaca ctacgttcct cagttggctc     480
aagccataaa gaggcatcat gaggccactg agacaaatc aatcaatcta aagggttata     540
tggtaggaaa tgccctgact gacgatttcc atgaccacta tggaatattt caatatatgt     600
ggaccactgg cttgatttct gatcaaacat acaagctact gaacattttc tgtgacttcg     660
agtcctttgt gcatacatct ccacagtgtg ataagattct tgacattgct agcactgaag     720
ctgggaacat tgattcgtat agcatcttca cacctacttg tcattcatct tttgcctcct     780
caaggaacaa agtggtgaaa aggcttcggt ctgttggaaa atggggggag caatacgatc     840
catgtaccga aaaacattca attgtatatt tcaatctgca tgaggtgcag aaggcacttc     900
```

```
acgtcaatcc ggtcattggc aaatccaaat gggagacctg cagtgaagtt attaacacca    960
actggaagga ctgtgaaaga tctgtattgc atatctatca tgaacttatt cagtatgggc   1020
ttcgtatatg gatgttcagt ggagacacag atgcagtgat ccagtaacaa tcaactagat   1080
acagcattga tgctctcaag cttccaacag tgaccccgtg gcatgcttgg tatgatgatg   1140
atggcgaggt tggtggttgg acccaagggt acaagggtct caactttgtg acagtaaggg   1200
gtgcgggtca tgaggttcct ctccatcgtc ccaagcaggc tcttacgctc atcaaatcat   1260
tcttggccgg gaggccaatg cctgtgctgt ctgatctacg cagcgatatg taatatgccg   1320
gacacatttg gtttcggaca cgaccagcac cacaagattc cagctcacca aggcagttcg   1380
gttgttaaaa ctccacacgt acttccacaa tataaggatg ccatagctg ttgccatttg     1440 taagtgctat tggcaccaat taatcccgtg agacagggaa acagttttcc tgccgctaat   1500
tgacactgca gcactgcctg ttaaattaat ctggaactaa ggataaagat gaattgaatt   1560
tcccaaaaaa aaaaaaaaaa                                                1580

<210> SEQ ID NO 10
<211> LENGTH: 436
<212> TYPE: PRT
<213> ORGANISM: Hordeum vulgare

<400> SEQUENCE: 10

Val Pro Arg Val Pro Gly Gln Ala Phe Asp Ala Ser Phe Ala His Tyr
  1               5                  10                  15

Ala Gly Tyr Val Thr Val Ser Glu Asp Arg Gly Ala Ala Leu Phe Tyr
                 20                  25                  30

Trp Phe Phe Glu Ala Ala His Asp Pro Ala Ser Lys Pro Leu Leu Leu
             35                  40                  45

Trp Leu Asn Gly Gly Pro Gly Cys Ser Ser Ile Ala Phe Gly Val Gly
         50                  55                  60

Glu Glu Val Gly Pro Phe His Val Asn Ala Asp Gly Lys Gly Val His
 65                  70                  75                  80

Met Asn Pro Tyr Ser Trp Asn Gln Val Ala Asn Ile Leu Phe Leu Asp
                 85                  90                  95

Ser Pro Val Gly Val Gly Tyr Ser Tyr Ser Asn Thr Ser Ala Asp Ile
                100                 105                 110

Leu Ser Asn Gly Asp Glu Arg Thr Ala Lys Asp Ser Leu Val Phe Leu
            115                 120                 125

Thr Lys Trp Leu Glu Arg Phe Pro Gln Tyr Lys Glu Arg Glu Phe Tyr
        130                 135                 140

Leu Thr Gly Glu Ser Tyr Ala Gly His Tyr Val Pro Gln Leu Ala Gln
145                 150                 155                 160

Ala Ile Lys Arg His His Glu Ala Thr Gly Asp Lys Ser Ile Asn Leu
                165                 170                 175

Lys Gly Tyr Met Val Gly Asn Ala Leu Thr Asp Asp Phe His Asp His
            180                 185                 190

Tyr Gly Ile Phe Gln Tyr Met Trp Thr Thr Gly Leu Ile Ser Asp Gln
        195                 200                 205

Thr Tyr Lys Leu Leu Asn Ile Phe Cys Asp Phe Glu Ser Phe Val His
    210                 215                 220

Thr Ser Pro Gln Cys Asp Lys Ile Leu Asp Ile Ala Ser Thr Glu Ala
225                 230                 235                 240

Gly Asn Ile Asp Ser Tyr Ser Ile Phe Thr Pro Thr Cys His Ser Ser
                245                 250                 255
```

-continued

```
Phe Ala Ser Ser Arg Asn Lys Val Val Lys Arg Leu Arg Ser Val Gly
            260                 265                 270

Lys Met Gly Glu Gln Tyr Asp Pro Cys Thr Glu Lys His Ser Ile Val
        275                 280                 285

Tyr Phe Asn Leu His Glu Val Gln Lys Ala Leu His Val Asn Pro Val
    290                 295                 300

Ile Gly Lys Ser Lys Trp Glu Thr Cys Ser Glu Val Ile Asn Thr Asn
305                 310                 315                 320

Trp Lys Asp Cys Glu Arg Ser Val Leu His Ile Tyr His Glu Leu Ile
                325                 330                 335

Gln Tyr Gly Leu Arg Ile Trp Met Phe Ser Gly Asp Thr Asp Ala Val
            340                 345                 350

Ile Pro Val Thr Ser Thr Arg Tyr Ser Ile Asp Ala Leu Lys Leu Pro
        355                 360                 365

Thr Val Thr Pro Trp His Ala Trp Tyr Asp Asp Gly Glu Val Gly
    370                 375                 380

Gly Trp Thr Gln Gly Tyr Lys Gly Leu Asn Phe Val Thr Val Arg Gly
385                 390                 395                 400

Ala Gly His Glu Val Pro Leu His Arg Pro Lys Gln Ala Leu Thr Leu
                405                 410                 415

Ile Lys Ser Phe Leu Ala Gly Arg Pro Met Pro Val Leu Ser Asp Leu
            420                 425                 430

Arg Ser Asp Met
        435

<210> SEQ ID NO 11
<211> LENGTH: 423
<212> TYPE: PRT
<213> ORGANISM: Triticum aestivum

<400> SEQUENCE: 11

Val Glu Pro Ser Gly His Ala Ala Asp Arg Ile Ala Arg Leu Pro Gly
  1               5                  10                  15

Gln Pro Ala Val Asp Phe Asp Met Tyr Ser Gly Tyr Ile Thr Val Asp
             20                  25                  30

Glu Gly Ala Gly Arg Ser Leu Phe Tyr Leu Leu Gln Glu Ala Pro Glu
         35                  40                  45

Asp Ala Gln Pro Ala Pro Leu Val Leu Trp Leu Asn Gly Gly Pro Gly
     50                  55                  60

Cys Ser Ser Val Ala Tyr Gly Ala Ser Glu Glu Leu Gly Ala Phe Arg
 65                  70                  75                  80

Val Lys Pro Arg Gly Ala Gly Leu Val Leu Asn Glu Tyr Arg Trp Asn
                 85                  90                  95

Lys Val Ala Asn Val Leu Phe Leu Asp Ser Pro Ala Gly Val Gly Phe
            100                 105                 110

Ser Tyr Thr Asn Thr Ser Ser Asp Ile Tyr Thr Ser Gly Asp Asn Arg
        115                 120                 125

Thr Ala His Asp Ser Tyr Ala Phe Leu Ala Lys Trp Phe Glu Arg Phe
    130                 135                 140

Pro His Tyr Lys Tyr Arg Asp Phe Tyr Ile Ala Gly Glu Ser Tyr Ala
145                 150                 155                 160

Gly His Tyr Val Pro Glu Leu Ser Gln Leu Val His Arg Ser Lys Asn
                165                 170                 175

Pro Val Ile Asn Leu Lys Gly Phe Met Val Gly Asn Gly Leu Ile Asp
```

|     |     |     |     |     | 180 |     |     |     |     | 185 |     |     |     |     | 190 |     |
| --- | --- | --- | --- | --- | --- | --- | --- | --- | --- | --- | --- | --- | --- | --- | --- | --- |
| Asp | Tyr | His | Asp | Tyr | Val | Gly | Thr | Phe | Glu | Phe | Trp | Trp | Asn | His | Gly |     |
|     |     |     |     | 195 |     |     |     |     | 200 |     |     |     |     | 205 |     |     |

Ile Val Ser Asp Asp Thr Tyr Arg Arg Leu Lys Glu Ala Cys Leu His
            210                 215                 220

Asp Ser Phe Ile His Pro Ser Pro Ala Cys Asp Ala Ala Thr Asp Val
225                 230                 235                 240

Ala Thr Ala Glu Gln Gly Asn Ile Asp Met Tyr Ser Leu Tyr Thr Pro
            245                 250                 255

Val Cys Asn Ile Thr Ser Ser Thr Gly Ser Tyr Asp Pro Cys Thr Glu
            260                 265                 270

Arg Tyr Ser Thr Ala Tyr Tyr Asn Arg Arg Asp Val Gln Met Ala Leu
            275                 280                 285

His Ala Asn Val Thr Gly Ala Met Asn Tyr Thr Trp Ala Thr Cys Ser
            290                 295                 300

Asp Thr Ile Asn Thr His Trp His Asp Ala Pro Arg Ser Met Leu Pro
305                 310                 315                 320

Ile Tyr Arg Glu Leu Ile Ala Ala Gly Leu Arg Ile Trp Val Phe Ser
            325                 330                 335

Gly Asp Thr Asp Ala Val Val Pro Leu Thr Ala Thr Arg Tyr Ser Ile
            340                 345                 350

Gly Ala Leu Gly Leu Pro Thr Thr Thr Ser Trp Tyr Pro Trp Tyr Asp
            355                 360                 365

Asp Gln Glu Val Gly Gly Trp Ser Gln Val Tyr Lys Gly Leu Thr Leu
            370                 375                 380

Val Ser Val Arg Gly Ala Gly His Glu Val Pro Leu His Arg Pro Arg
385                 390                 395                 400

Gln Ala Leu Val Leu Phe Gln Tyr Phe Leu Gln Gly Lys Pro Met Pro
            405                 410                 415

Gly Gln Thr Lys Asn Ala Thr
            420

```
<210> SEQ ID NO 12
<211> LENGTH: 1485
<212> TYPE: DNA
<213> ORGANISM: Pisum sativum

<400> SEQUENCE: 12
gaaacttctc ttcttctatc ctttctcatt attctctcac actttgtggt tgaaatccat      60
ggaaaaaaca aacaagttga agctcttgac aatcttcaca aagcagaata catagaaaat     120
tcagaaattg ataagagtga atttgaagta caagagattg tgtatgacat tgatgccatt     180
gctgattctc aaaagggtgt caagagagaat gatagaatca aaaagcttcc tggtcaaccc    240
tttgtgaaat tctctcaatt tggagggtat gttacattgg ataaattgag tggtagtgcg     300
ttttactatt actttgttga agctcatcaa tctaaagaaa cacctccact tcttctttgg     360
ctcaatggag gtcctggatg ttcatctcta gcttatggag caatgcaaga attgggacct     420
tttagagtaa acagtgatgg caaaacactt caccaaaata gatactcatg gaattatgct     480
gcaaatgttt tgttcttgga gtctccagtt ggagtaggat tttcttactc aaacaaatca     540
acagaatata gtagcaatgg agacaagaaa acagctatag ataactattt attttggta    600 aattggttgg aaagatttcc agaatataaa aatagagatt tttatatttc tggagaaagc    660
tatgctggac attatgttcc tcaacttgca cataccatcc tctatcataa taaaaggca     720
```

```
aataaaacaa tcattaacct caaaggaatc ttgatagggaa atgcagtgat ccatgatact    780
acagactcaa caggaatgta tgattttctt gctactcatg ctatcatctc agacaaagca    840
gcttatgatg tcaacaaagt ttgcgatttc tcgtcatcag ataatctcac tgctgaatgc    900
aattcagctg ctgatgaagt taatgaagat attgcattca tcgatttgta taacatttat    960
gctccactat gcaagaatga gaatctcact tccaagccca aaagaacac tattgtgact    1020 gatccatgca gtaagaatta tgtgtatgct tatcttaata gacaagatgt tcaagaggct    1080
attcatgcta atgtcacaaa actcaaatat gaatggagtc catgcagtgg tgtcattaga    1140
aaatgggttg atagctctcc aacagttctt cctcttttac atgaattcct caataatggc    1200
cttagagttt ggattttcag cggtgacacg gatggaaggg ttcctgttac ttcgactaag    1260
tattcgatta gaagatgaa ccttcctgtt aaaactgttt ggcacccttg gttcgcctat    1320
ggagaagttg gtggctatac tgaagtatac aagggagacc taacatttgt tacagtgaga    1380
gaagcaggac atcaagtgcc aagttatcaa ccagcaagag ctcttacttt gattaaacat    1440
ttcttggatg gcactcctct tccttctcca aaaataaaag catag                    1485
```

<210> SEQ ID NO 13
<211> LENGTH: 494
<212> TYPE: PRT
<213> ORGANISM: Pisum sativum

<400> SEQUENCE: 13

```
Glu Thr Ser Leu Leu Leu Ser Phe Leu Ile Ile Leu Ser His Phe Val
  1               5                  10                  15

Val Glu Ile His Gly Lys Asn Lys Gln Val Glu Ala Leu Asp Asn Leu
             20                  25                  30

His Lys Ala Glu Tyr Ile Glu Asn Ser Glu Ile Asp Lys Ser Glu Phe
         35                  40                  45

Glu Val Gln Glu Ile Val Tyr Asp Ile Asp Ala Ile Ala Asp Ser Gln
     50                  55                  60

Lys Gly Val Lys Glu Asn Asp Arg Ile Lys Lys Leu Pro Gly Gln Pro
 65                  70                  75                  80

Phe Val Lys Phe Ser Gln Phe Gly Gly Tyr Val Thr Leu Asp Lys Leu
                 85                  90                  95

Ser Gly Ser Ala Phe Tyr Tyr Tyr Phe Val Glu Ala His Gln Ser Lys
            100                 105                 110

Glu Thr Pro Pro Leu Leu Leu Trp Leu Asn Gly Gly Pro Gly Cys Ser
        115                 120                 125

Ser Leu Ala Tyr Gly Ala Met Gln Glu Leu Gly Pro Phe Arg Val Asn
    130                 135                 140

Ser Asp Gly Lys Thr Leu His Gln Asn Arg Tyr Ser Trp Asn Tyr Ala
145                 150                 155                 160

Ala Asn Val Leu Phe Leu Glu Ser Pro Val Gly Val Gly Phe Ser Tyr
                165                 170                 175

Ser Asn Lys Ser Thr Glu Tyr Ser Ser Asn Gly Asp Lys Lys Thr Ala
            180                 185                 190

Ile Asp Asn Tyr Leu Phe Leu Val Asn Trp Leu Glu Arg Phe Pro Glu
        195                 200                 205

Tyr Lys Asn Arg Asp Phe Tyr Ile Ser Gly Glu Ser Tyr Ala Gly His
    210                 215                 220

Tyr Val Pro Gln Leu Ala His Thr Ile Leu Tyr His Asn Lys Lys Ala
225                 230                 235                 240
```

```
Asn Lys Thr Ile Ile Asn Leu Lys Gly Ile Leu Ile Gly Asn Ala Val
            245                 250                 255

Ile His Asp Thr Thr Asp Ser Thr Gly Met Tyr Asp Phe Leu Ala Thr
            260                 265                 270

His Ala Ile Ile Ser Asp Lys Ala Ala Tyr Asp Val Asn Lys Val Cys
            275                 280                 285

Asp Phe Ser Ser Asp Asn Leu Thr Ala Glu Cys Asn Ser Ala Ala
    290                 295                 300

Asp Glu Val Asn Glu Asp Ile Ala Phe Ile Asp Leu Tyr Asn Ile Tyr
305                 310                 315                 320

Ala Pro Leu Cys Lys Asn Glu Asn Leu Thr Ser Lys Pro Lys Asn
            325                 330                 335

Thr Ile Val Thr Asp Pro Cys Ser Lys Asn Tyr Val Tyr Ala Tyr Leu
            340                 345                 350

Asn Arg Gln Asp Val Gln Glu Ala Ile His Ala Asn Val Thr Lys Leu
            355                 360                 365

Lys Tyr Glu Trp Ser Pro Cys Ser Gly Val Ile Arg Lys Trp Val Asp
    370                 375                 380

Ser Ser Pro Thr Val Leu Pro Leu Leu His Glu Phe Leu Asn Asn Gly
385                 390                 395                 400

Leu Arg Val Trp Ile Phe Ser Gly Asp Thr Asp Gly Arg Val Pro Val
                405                 410                 415

Thr Ser Thr Lys Tyr Ser Ile Lys Lys Met Asn Leu Pro Val Lys Thr
            420                 425                 430

Val Trp His Pro Trp Phe Ala Tyr Gly Glu Val Gly Tyr Thr Glu
            435                 440                 445

Val Tyr Lys Gly Asp Leu Thr Phe Val Thr Val Arg Glu Ala Gly His
    450                 455                 460

Gln Val Pro Ser Tyr Gln Pro Ala Arg Ala Leu Thr Leu Ile Lys His
465                 470                 475                 480

Phe Leu Asp Gly Thr Pro Leu Pro Ser Pro Lys Ile Lys Ala
            485                 490
```

<210> SEQ ID NO 14
<211> LENGTH: 1488
<212> TYPE: DNA
<213> ORGANISM: Medicago truncatula

<400> SEQUENCE: 14

| | | |
|---|---|---|
| atgaagaagg tttctcttta tgcttgttta ttactcaact tgagccttt ggttatttt | 60 |
| ccatatagca aagctagtca agctgataaa ttcaatgagt ttattctgtc tagaaaatct | 120 |
| cagaatcctc ccaagacact ttcttgggaa gagggagatg cattgaaaac acattctttt | 180 |
| tctgctgctt atgttgcacc acctcaagag gagctaagac tagctgacaa gatcgtcaca | 240 |
| ttgcctggtc aacccatgg agtgaatttt gaccaatatt caggctatgt cacagttgat | 300 |
| cctgaggctg aagagaact tttctattat tttgtggaat ctccacataa ctcttatact | 360 |
| aaacccttaa tattgtggct taatggagga cctggttgtt cctcactggg atatggagcc | 420 |
| tttgaggagc tcggaccctt cagagtcaac tctgatgcaa aacattata ccgtaaccca | 480 |
| tatgcttgga atgaagtggc aaatgtactc ttcttggaat ctccagcagg ggtaggattt | 540 |
| tcctactcaa acacatcatc ggactatgac aattcaggag ataagtccac tgctaaagat | 600 |
| gcctatgtct tcctaatcaa ctggctggag agatttccac agtacaaaac cagagatttt | 660 |
| tacataactg gagagagtta tgccggtcat tatgttcctc aacttgcatc cactattctt | 720 |

-continued

```
tacaacaata aactctataa caacaccatt attaacctca aaggcatttc tatagggaat    780
gcttggattg atgatgcgac gaatttaaag gggatatatg ataacttgtg gactcatgct    840
ttaaactcag atcaaactca tgagttgatt gagaagtact gtgacttcac taaagaaaat    900
gtttcagcaa tttgtaacaa tgcaactgat aaggccttcg ttgagacagg aaagatagac    960
atctataaca tccatgcgcc attgtgtcat gactcttctc tgaaaaatgg ttctagtact   1020
ggttacgtaa gcaatgattt tgacccttgt tctgattact atgttactgc ctatctaaat   1080
agaccagaag ttcaaaaggc tcttcatgca aaacctacaa attggaccca ttgcactcat   1140
cttcttacta cctggaaaga cagtccagct accgtcctac ccaccgtcaa gtatctcatt   1200
gatagcggca ttaaattatg gatatacagt ggtgatacag atgtagtggt tccaaccaca   1260
tcttcaagat atttaatcaa cacccttaaa cttccaatca actctgcttg gcgtccgtgg   1320
tattctggaa aagagattgg agggtatgtt gtgggataca aaggattgac atttgttaca   1380
gtgagaggag caggacatct tgttccaagc tggcaacctg aacgtgcttt gactttgatc   1440
tcatcattcc tctatggaat cctgccttct ggttcaccgt cgaattaa               1488

<210> SEQ ID NO 15
<211> LENGTH: 495
<212> TYPE: PRT
<213> ORGANISM: Medicago truncatula

<400> SEQUENCE: 15

Met Lys Lys Val Ser Leu Tyr Ala Cys Leu Leu Asn Leu Ser Leu
 1               5                  10                  15

Leu Val Ile Phe Pro Tyr Ser Lys Ala Ser Gln Ala Asp Lys Phe Asn
                20                  25                  30

Glu Phe Ile Leu Ser Arg Lys Ser Gln Asn Pro Pro Lys Thr Leu Ser
            35                  40                  45

Trp Glu Glu Gly Asp Ala Leu Lys Thr His Ser Phe Ser Ala Ala Tyr
        50                  55                  60

Val Ala Pro Pro Gln Glu Glu Leu Arg Leu Ala Asp Lys Ile Val Thr
    65                  70                  75                  80

Leu Pro Gly Gln Pro Tyr Gly Val Asn Phe Asp Gln Tyr Ser Gly Tyr
                85                  90                  95

Val Thr Val Asp Pro Glu Ala Gly Arg Glu Leu Phe Tyr Tyr Phe Val
            100                 105                 110

Glu Ser Pro His Asn Ser Tyr Thr Lys Pro Leu Ile Leu Trp Leu Asn
        115                 120                 125

Gly Gly Pro Gly Cys Ser Ser Leu Gly Tyr Gly Ala Phe Glu Glu Leu
    130                 135                 140

Gly Pro Phe Arg Val Asn Ser Asp Gly Lys Thr Leu Tyr Arg Asn Pro
145                 150                 155                 160

Tyr Ala Trp Asn Glu Val Ala Asn Val Leu Phe Leu Glu Ser Pro Ala
                165                 170                 175

Gly Val Gly Phe Ser Tyr Ser Asn Thr Ser Ser Asp Tyr Asp Asn Ser
            180                 185                 190

Gly Asp Lys Ser Thr Ala Lys Asp Ala Tyr Val Phe Leu Ile Asn Trp
        195                 200                 205

Leu Glu Arg Phe Pro Gln Tyr Lys Thr Arg Asp Phe Tyr Ile Thr Gly
    210                 215                 220

Glu Ser Tyr Ala Gly His Tyr Val Pro Gln Leu Ala Ser Thr Ile Leu
225                 230                 235                 240
```

```
Tyr Asn Asn Lys Leu Tyr Asn Asn Thr Ile Ile Asn Leu Lys Gly Ile
            245                 250                 255

Ser Ile Gly Asn Ala Trp Ile Asp Asp Ala Thr Asn Leu Lys Gly Ile
            260                 265                 270

Tyr Asp Asn Leu Trp Thr His Ala Leu Asn Ser Asp Gln Thr His Glu
            275                 280                 285

Leu Ile Glu Lys Tyr Cys Asp Phe Thr Lys Glu Asn Val Ser Ala Ile
        290                 295                 300

Cys Asn Asn Ala Thr Asp Lys Ala Phe Val Glu Thr Gly Lys Ile Asp
305                 310                 315                 320

Ile Tyr Asn Ile His Ala Pro Leu Cys His Asp Ser Ser Leu Lys Asn
            325                 330                 335

Gly Ser Ser Thr Gly Tyr Val Ser Asn Asp Phe Asp Pro Cys Ser Asp
            340                 345                 350

Tyr Tyr Val Thr Ala Tyr Leu Asn Arg Pro Glu Val Gln Lys Ala Leu
            355                 360                 365

His Ala Lys Pro Thr Asn Trp Thr His Cys Thr His Leu Leu Thr Thr
        370                 375                 380

Trp Lys Asp Ser Pro Ala Thr Val Leu Pro Thr Val Lys Tyr Leu Ile
385                 390                 395                 400

Asp Ser Gly Ile Lys Leu Trp Ile Tyr Ser Gly Asp Thr Asp Val Val
            405                 410                 415

Val Pro Thr Thr Ser Ser Arg Tyr Leu Ile Asn Thr Leu Lys Leu Pro
            420                 425                 430

Ile Asn Ser Ala Trp Arg Pro Trp Tyr Ser Gly Lys Glu Ile Gly Gly
            435                 440                 445

Tyr Val Val Gly Tyr Lys Gly Leu Thr Phe Val Thr Val Arg Gly Ala
        450                 455                 460

Gly His Leu Val Pro Ser Trp Gln Pro Glu Arg Ala Leu Thr Leu Ile
465                 470                 475                 480

Ser Ser Phe Leu Tyr Gly Ile Leu Pro Ser Gly Ser Pro Ser Asn
            485                 490                 495

<210> SEQ ID NO 16
<211> LENGTH: 1278
<212> TYPE: DNA
<213> ORGANISM: Arabidopsis thaliana

<400> SEQUENCE: 16
atgatcaagg cacttccagg gcaaccgcaa gtaggattct cacagttttc gggttatgtg        60
actgtgaacg agtcacatgg tcgatcactt ttctactggc ttacagagtc cccttcttct       120
tctcacacca aaccacttct tctttggctc aatggaggac cgggttgctc atcgattggt       180
tatggagctt cggaggaaat tggaccgttt cggatcaata aaaccggttc taatctctat       240
ctcaacaagt ttacgtggaa cacagaagcg aatattttgt ttcttgaatc gccggctgga       300
gttggatttt cgtacactaa cacaagctct gatcttaaag attctgggga cgaacggact       360
gctcaggaaa atttgatatt tctaattaaa tggatgtcga gatttcctca gtaccaatat       420
agagatttct acattgttgg tgaaagctac gctggtcatt atgttcctca gcttgccaaa       480
aagatccatc tctacaacaa agctttcaac aatacaccca tcattaacct caaaggattc       540
atggtgggaa atgagagatat ggacaagcat tacgacagat taggagccgc catgtatgcg       600
tggtcacacg caatgatctc tgacaaaact tacaagtcta tcctcaaaca ctgcagcttc       660
```

```
actgcggata aaacctcgga caagtgcaat tgggcactct acttcgccta cagagagttt    720
ggcaaagtca atgggtacag catctactca ccctcatgtg tacatcaaac caaccagacc    780
aagttcctgc atggacggct tttggtagag gaatacgagt acgacccttg taccgaaagc    840
tacgctgaga tatattacaa ccgtcctgat gtgcaacgag ctatgcacgc taatcttacc    900
tccattcctt ataagtggac attgtgcaat atggttgtga ataacaactg gaaagattcc    960
gagttttcaa tgttgccgat atacaaggaa ctcactccg ctggtttgag gatctgggtc    1020
tttagtggcg atacagacgc agtggttcca gtgactggga ctcgacttgc cctcagtaaa    1080
ctcaatcttc cggtgaaaac tccctggtac ccttggtact ccgaaaagca ggtgggagga    1140
tggacagagg tatatgaggg gcttaccttt gcgacgataa aggggcggg ccacgaagtg    1200 ccggtgttgc aacccgagcg tgctctcact cttttaagat cgttcttggc cggcaaagag    1260
cttccaagat cttattag                                                  1278
```

<210> SEQ ID NO 17
<211> LENGTH: 425
<212> TYPE: PRT
<213> ORGANISM: Arabidopsis thaliana

<400> SEQUENCE: 17

```
Met Ile Lys Ala Leu Pro Gly Gln Pro Gln Val Gly Phe Ser Gln Phe
  1               5                  10                  15

Ser Gly Tyr Val Thr Val Asn Glu Ser His Gly Arg Ser Leu Phe Tyr
             20                  25                  30

Trp Leu Thr Glu Ser Pro Ser Ser His Thr Lys Pro Leu Leu Leu
         35                  40                  45

Trp Leu Asn Gly Gly Pro Gly Cys Ser Ser Ile Gly Tyr Gly Ala Ser
     50                  55                  60

Glu Glu Ile Gly Pro Phe Arg Ile Asn Lys Thr Gly Ser Asn Leu Tyr
 65                  70                  75                  80

Leu Asn Lys Phe Thr Trp Asn Thr Glu Ala Asn Ile Leu Phe Leu Glu
                 85                  90                  95

Ser Pro Ala Gly Val Gly Phe Ser Tyr Thr Asn Thr Ser Ser Asp Leu
            100                 105                 110

Lys Asp Ser Gly Asp Glu Arg Thr Ala Gln Glu Asn Leu Ile Phe Leu
        115                 120                 125

Ile Lys Trp Met Ser Arg Phe Pro Gln Tyr Gln Tyr Arg Asp Phe Tyr
    130                 135                 140

Ile Val Gly Glu Ser Tyr Ala Gly His Tyr Val Pro Gln Leu Ala Lys
145                 150                 155                 160

Lys Ile His Leu Tyr Asn Lys Ala Phe Asn Asn Thr Pro Ile Ile Asn
                165                 170                 175

Leu Lys Gly Phe Met Val Gly Asn Gly Asp Met Asp Lys His Tyr Asp
            180                 185                 190

Arg Leu Gly Ala Ala Met Tyr Ala Trp Ser His Ala Met Ile Ser Asp
        195                 200                 205

Lys Thr Tyr Lys Ser Ile Leu Lys His Cys Ser Phe Thr Ala Asp Lys
    210                 215                 220

Thr Ser Asp Lys Cys Asn Trp Ala Leu Tyr Phe Ala Tyr Arg Glu Phe
225                 230                 235                 240

Gly Lys Val Asn Gly Tyr Ser Ile Tyr Ser Pro Ser Cys Val His Gln
                245                 250                 255

Thr Asn Gln Thr Lys Phe Leu His Gly Arg Leu Leu Val Glu Glu Tyr
```

```
                   260                 265                 270
Glu Tyr Asp Pro Cys Thr Glu Ser Tyr Ala Glu Ile Tyr Tyr Asn Arg
            275                 280                 285
Pro Asp Val Gln Arg Ala Met His Ala Asn Leu Thr Ser Ile Pro Tyr
        290                 295                 300
Lys Trp Thr Leu Cys Asn Met Val Val Asn Asn Trp Lys Asp Ser
305                 310                 315                 320
Glu Phe Ser Met Leu Pro Ile Tyr Lys Glu Leu Thr Ala Ala Gly Leu
                325                 330                 335
Arg Ile Trp Val Phe Ser Gly Asp Thr Asp Ala Val Val Pro Val Thr
            340                 345                 350
Gly Thr Arg Leu Ala Leu Ser Lys Leu Asn Leu Pro Val Lys Thr Pro
        355                 360                 365
Trp Tyr Pro Trp Tyr Ser Glu Lys Gln Val Gly Trp Thr Glu Val
370                 375                 380
Tyr Glu Gly Leu Thr Phe Ala Thr Ile Arg Gly Ala Gly His Glu Val
385                 390                 395                 400
Pro Val Leu Gln Pro Glu Arg Ala Leu Thr Leu Leu Arg Ser Phe Leu
                405                 410                 415
Ala Gly Lys Glu Leu Pro Arg Ser Tyr
                420                 425

<210> SEQ ID NO 18
<211> LENGTH: 1422
<212> TYPE: DNA
<213> ORGANISM: Arabidopsis thaliana

<400> SEQUENCE: 18
atggcaatgg caaaactcgc aattttcacc actcttatgg ccatactcgt aatgacatct      60
caaggaagga ttccaacaga aggaggagag aaagaagcag aggctgacag aattacgtca     120
cttccaggtc agcctaacgt cacgttcgag cagttttccg gctacgtcac cgtcgataaa     180
ctctccggaa gatcactctt ttattggctc actgaagctt ctgacctccc tctctccaaa     240
cctctcgtaa tttggctcaa cggaggaccg ggatgttcgt cggtagcgta cggtgcgtcg     300
gaggagattg gaccattcag gataagcaaa ggtggttccg gtttgtatct caacaagttc     360
gcatggaact caatctccaa tctcttgttc ctcgaagctc ccgccggcgt cggcttctct     420
tacactaacc gctcctccga tctcttcaac accggtgatc gccgtaccgc caaagattca     480
cttcagtttc ttattcaatg gcttcaccgg tttccgagat acaaccaccg ggaaatctac     540
atcaccggcg agagttacgc cggacattac gttcctcagc tggccaaaga gatcatgaat     600
tacaacaaac gatcaaagaa tccgttaaat ctcaaaggaa tcatggttgg aaacgcggtg     660
acggacaatc actatgataa cctaggaacg gtttcgtatt ggtggagcca cgcgatgatc     720
tctgatcgga cgtatcatca gttgataagc acttgcgatt tagtcgtca gaaggaatct     780 gatgaatgcg aaacccttta ttcttacgct atggagcagg agtttggtaa cattgatcag     840
tacaacatct atgcgccgcc gtgtaacaag tcaagcgacg tggtggtag ctacaatggt      900 tcttccggcc gcggagtat gcggcttcct caccttcccc actccgtatt gaggaaaatt     960
tccggttatg atccatgtac cgagagatat gcagagatct attataaccg gcctgatgtt    1020
cagaaagctc ttcacgccaa caccaccaag attccgtata atggacagc ttgcagtgag    1080 gtgctaaacc ggaattggaa cgacacagat tcaacggttc ccctatata ccggaaatg     1140 attgccggcg gaattagagt ttgggttttc agtggtgacg tcgattcagt tgtaccagtg    1200
```

```
acagctacta gatactcact agcaagactt agtttgagta ccaaacttcc ttggtatcct   1260
tggtatgtca agaaacaggt tggaggatgg acggaagtgt atgaaggact aacgttcgtg   1320
acggttagag gagcaggtca cgaggtgcca ttgttcaagc cacgtgctgc ttttgagctt   1380
tttaagtatt tcttgagagg caagccactt ccaaaggctt aa                      1422
```

<210> SEQ ID NO 19
<211> LENGTH: 473
<212> TYPE: PRT
<213> ORGANISM: Arabidopsis thaliana

<400> SEQUENCE: 19

```
Met Ala Met Ala Lys Leu Ala Ile Phe Thr Thr Leu Met Ala Ile Leu
  1               5                  10                  15

Val Met Thr Ser Gln Gly Arg Ile Pro Thr Glu Gly Gly Lys Glu
             20                  25                  30

Ala Glu Ala Asp Arg Ile Thr Ser Leu Pro Gly Gln Pro Asn Val Thr
         35                  40                  45

Phe Glu Gln Phe Ser Gly Tyr Val Thr Val Asp Lys Leu Ser Gly Arg
     50                  55                  60

Ser Leu Phe Tyr Trp Leu Thr Glu Ala Ser Asp Leu Pro Leu Ser Lys
 65                  70                  75                  80

Pro Leu Val Ile Trp Leu Asn Gly Gly Pro Gly Cys Ser Ser Val Ala
                 85                  90                  95

Tyr Gly Ala Ser Glu Glu Ile Gly Pro Phe Arg Ile Ser Lys Gly Gly
            100                 105                 110

Ser Gly Leu Tyr Leu Asn Lys Phe Ala Trp Asn Ser Ile Ser Asn Leu
        115                 120                 125

Leu Phe Leu Glu Ala Pro Ala Gly Val Gly Phe Ser Tyr Thr Asn Arg
    130                 135                 140

Ser Ser Asp Leu Phe Asn Thr Gly Asp Arg Arg Thr Ala Lys Asp Ser
145                 150                 155                 160

Leu Gln Phe Leu Ile Gln Trp Leu His Arg Phe Pro Arg Tyr Asn His
                165                 170                 175

Arg Glu Ile Tyr Ile Thr Gly Glu Ser Tyr Ala Gly His Tyr Val Pro
            180                 185                 190

Gln Leu Ala Lys Glu Ile Met Asn Tyr Asn Lys Arg Ser Lys Asn Pro
        195                 200                 205

Leu Asn Leu Lys Gly Ile Met Val Gly Asn Ala Val Thr Asp Asn His
    210                 215                 220

Tyr Asp Asn Leu Gly Thr Val Ser Tyr Trp Trp Ser His Ala Met Ile
225                 230                 235                 240

Ser Asp Arg Thr Tyr His Gln Leu Ile Ser Thr Cys Asp Phe Ser Arg
                245                 250                 255

Gln Lys Glu Ser Asp Glu Cys Glu Thr Leu Tyr Ser Tyr Ala Met Glu
            260                 265                 270

Gln Glu Phe Gly Asn Ile Asp Gln Tyr Asn Ile Tyr Ala Pro Pro Cys
        275                 280                 285

Asn Lys Ser Ser Asp Gly Gly Ser Tyr Asn Gly Ser Gly Arg
    290                 295                 300

Arg Ser Met Arg Leu Pro His Leu Pro His Ser Val Leu Arg Lys Ile
305                 310                 315                 320

Ser Gly Tyr Asp Pro Cys Thr Glu Arg Tyr Ala Glu Ile Tyr Tyr Asn
                325                 330                 335
```

```
Arg Pro Asp Val Gln Lys Ala Leu His Ala Asn Thr Thr Lys Ile Pro
        340                 345                 350

Tyr Lys Trp Thr Ala Cys Ser Glu Val Leu Asn Arg Asn Trp Asn Asp
        355                 360                 365

Thr Asp Ser Thr Val Leu Pro Ile Tyr Arg Glu Met Ile Ala Gly Gly
        370                 375                 380

Ile Arg Val Trp Val Phe Ser Gly Asp Val Asp Ser Val Val Pro Val
385                 390                 395                 400

Thr Ala Thr Arg Tyr Ser Leu Ala Arg Leu Ser Leu Ser Thr Lys Leu
                405                 410                 415

Pro Trp Tyr Pro Trp Tyr Val Lys Lys Gln Val Gly Gly Trp Thr Glu
                420                 425                 430

Val Tyr Glu Gly Leu Thr Phe Val Thr Val Arg Gly Ala Gly His Glu
                435                 440                 445

Val Pro Leu Phe Lys Pro Arg Ala Ala Phe Glu Leu Phe Lys Tyr Phe
                450                 455                 460

Leu Arg Gly Lys Pro Leu Pro Lys Ala
465                 470

<210> SEQ ID NO 20
<211> LENGTH: 1359
<212> TYPE: DNA
<213> ORGANISM: Arabidopsis thaliana

<400> SEQUENCE: 20
atggctcgac tccttctcct cttcttcttc ttccttattc tactccatta cgcttcttgt      60
tccagacacg aacaagaaaa agaccgaatc tttcaccttc ccggtgaacc aaacgatgtc     120
tccttctctc acttctctgg ttacattacc gtcaacgagt cagcaggaag agcactattc     180
tactggctca ctgagtcacc accgagtgaa aaccctgagt ctaagcctct tgtcctctgg     240
ctcaacggtg gacctggttg ttcctccgta gcttacggtg ccgctgaaga aatcggacct     300
tttagaatca atcctgatgg caaaactctt taccacaatc cttactcttg aacaaattg      360 gcgaatttgc tcttccttga atctcctgct ggtgttggtt tctcgtattc gaatactacc     420
tccgatttgt atactgccgg agatcagaga actgcggaag atgcttatgt gtttcttgtg     480
aaatggtttg agaggtttcc tcaatacaaa cacagagagt tctacattgc tggagaaagc     540
tatgcaggtc attatgttcc tcagttgtca cagattgttt atgagaaacg caatccagct     600
atcaacttta aaggcttcat tgttgggaat gctgtgattg atgactacca tgattacgtg     660
ggtttatttg aatattggtg ggctcatggg ttgatatctg atctcactta ccacaactta     720
cggatcacgt gtgaatttgg atcatccgag cacccgtcct ctaaatgcac caaggccatg     780
gaagctgcag acttggagca aggcaatatt gatccttata gcatttacac tgtcacttgt     840
aaaaaggagg ctgcagctct taggtctcgc ttctcgagag ttcgtcatcc atggatgtgg     900
agagcctatg acccttgcac agagaaatac tccggcatgt atttcaattc tccggaggtt     960
caaaaggcta tgcatgctaa taacaggact agcttatc catggaaagg gtgcagtgac    1020
atcgttggag agaaatgggc agattctcct ctgtctatgc ttccaatcta caagaactc    1080 atcgccgcag gtctcaggat atgggttttc agcggagaca ctgattcagt ggttcccatt    1140
actggaacac gatactccat tagagccctc aagttacaac cactctccaa atggtaccct    1200
tggaacgatg atggacaggt tggtggatgg agccaagttt acaaagggct gactctggtg    1260
acaatacatg gagcaggaca tgaggtacct cttttccgcc ctcgtcgagc ttttcttctt    1320
```
tttcagtcgt tttctcgacaa caagccattg ccaatgtaa                    1359

<210> SEQ ID NO 21
<211> LENGTH: 452
<212> TYPE: PRT
<213> ORGANISM: Arabidopsis thaliana

<400> SEQUENCE: 21

Met Ala Arg Leu Leu Leu Phe Phe Phe Leu Ile Leu Leu His
1               5                   10                  15

Tyr Ala Ser Cys Ser Arg His Glu Gln Glu Lys Asp Arg Ile Phe His
            20                  25                  30

Leu Pro Gly Glu Pro Asn Asp Val Ser Phe Ser His Phe Ser Gly Tyr
        35                  40                  45

Ile Thr Val Asn Glu Ser Ala Gly Arg Ala Leu Phe Tyr Trp Leu Thr
    50                  55                  60

Glu Ser Pro Pro Ser Glu Asn Pro Glu Ser Lys Pro Leu Val Leu Trp
65                  70                  75                  80

Leu Asn Gly Gly Pro Gly Cys Ser Ser Val Ala Tyr Gly Ala Ala Glu
                85                  90                  95

Glu Ile Gly Pro Phe Arg Ile Asn Pro Asp Gly Lys Thr Leu Tyr His
            100                 105                 110

Asn Pro Tyr Ser Trp Asn Lys Leu Ala Asn Leu Leu Phe Leu Glu Ser
        115                 120                 125

Pro Ala Gly Val Gly Phe Ser Tyr Ser Asn Thr Thr Ser Asp Leu Tyr
    130                 135                 140

Thr Ala Gly Asp Gln Arg Thr Ala Glu Asp Ala Tyr Val Phe Leu Val
145                 150                 155                 160

Lys Trp Phe Glu Arg Phe Pro Gln Tyr Lys His Arg Glu Phe Tyr Ile
                165                 170                 175

Ala Gly Glu Ser Tyr Ala Gly His Tyr Val Pro Gln Leu Ser Gln Ile
            180                 185                 190

Val Tyr Glu Lys Arg Asn Pro Ala Ile Asn Phe Lys Gly Phe Ile Val
        195                 200                 205

Gly Asn Ala Val Ile Asp Asp Tyr His Asp Tyr Val Gly Leu Phe Glu
    210                 215                 220

Tyr Trp Trp Ala His Gly Leu Ile Ser Asp Leu Thr Tyr His Asn Leu
225                 230                 235                 240

Arg Ile Thr Cys Glu Phe Gly Ser Ser Glu His Pro Ser Ser Lys Cys
                245                 250                 255

Thr Lys Ala Met Glu Ala Ala Asp Leu Glu Gln Gly Asn Ile Asp Pro
            260                 265                 270

Tyr Ser Ile Tyr Thr Val Thr Cys Lys Lys Glu Ala Ala Ala Leu Arg
        275                 280                 285

Ser Arg Phe Ser Arg Val Arg His Pro Trp Met Trp Arg Ala Tyr Asp
    290                 295                 300

Pro Cys Thr Glu Lys Tyr Ser Gly Met Tyr Phe Asn Ser Pro Glu Val
305                 310                 315                 320

Gln Lys Ala Met His Ala Asn Ile Thr Gly Leu Ala Tyr Pro Trp Lys
                325                 330                 335

Gly Cys Ser Asp Ile Val Gly Glu Lys Trp Ala Asp Ser Pro Leu Ser
            340                 345                 350

Met Leu Pro Ile Tyr Lys Glu Leu Ile Ala Ala Gly Leu Arg Ile Trp
        355                 360                 365

```
Val Phe Ser Gly Asp Thr Asp Ser Val Val Pro Ile Thr Gly Thr Arg
        370                 375                 380

Tyr Ser Ile Arg Ala Leu Lys Leu Gln Pro Leu Ser Lys Trp Tyr Pro
385                 390                 395                 400

Trp Asn Asp Asp Gly Gln Val Gly Gly Trp Ser Gln Val Tyr Lys Gly
                405                 410                 415

Leu Thr Leu Val Thr Ile His Gly Ala Gly His Glu Val Pro Leu Phe
            420                 425                 430

Arg Pro Arg Ala Phe Leu Leu Phe Gln Ser Phe Leu Asp Asn Lys
        435                 440                 445

Pro Leu Pro Met
    450

<210> SEQ ID NO 22
<211> LENGTH: 1380
<212> TYPE: DNA
<213> ORGANISM: Arabidopsis thaliana

<400> SEQUENCE: 22
atggattact ctttccttct aatcattctc ttactcacaa tctctacttc atgttgtgct      60
gctccttctt cttatgtgga agaacaattg agagacagaa tcagtaactt acctggacaa     120
cctagtaatg tcgattttag acagtactca ggctatgtca ctgtgcatga agaacgtgga     180
agagctttgt tctactggtt ggtcgagtct ccgttggccc gtgacccaaa gtctagacct     240
ttggttctgt ggctcaatgg tggccctggt tgttcttctg ttgcttatgg tgctgctgaa     300
gaaattggac cttttcgtgt tggttctgat ggcaagactc ttcattccaa actttatgct     360
tggaataaat tggcaaactt gctattcttg agtctccag ctggagttgg tttctcatat     420
tcaaacacaa cttcagatct ttacacaacc ggtgatcaga aacagctga ggattcgtac     480
atatttcttg tcaactggtt tgagaggttt ccacaataca agcataggga gttttacatt     540
gttggagaaa gctatgcagg tcattttgtt cctcaactgt ctaaacttgt ccatgaaagg     600
aacaagggct tcaagaaccc ggctataaac ctcaaaggtt tatggtggg aaatgctgtt     660
acagatgact atcatgatta tataggaaca tttgaatact ggtggaatca cggtctcata     720
tccgattcca cgtatcacca actaaagacc gcgtgctact cagtatcatc tcagcatcct     780
tcaatgcagt gtatggtggc tctgagaaat gccgaattag agcaaggaaa tatcgatcca     840
tatagcattt tcaccaaacc ttgcaacagt actgtggcac ttaagagatt cttaaaggt     900
cgctacccat ggatgtcaag agcttatgat ccttgtacag agagatattc gaatgtgtat     960
tttaaccgct tggacgttca gaaggctctc cacgcaaatg tcactcgctt atcttacccc    1020
tggaaagcat gcagtgacat tgtaggaagc tattgggacg attctcctct gtctatgctt    1080
cctatataca aagaattgat tactgcaggt ctcaaaatat gggtcttcag tgggatacc    1140
gatgctgttg ttcctataac cgctacccga tactctgtag atgcactgaa gctagcaacc    1200
atcacgaact ggtacccgtg gtacgaccat ggcaaggtag gtgggtggag tcaagtttac    1260
aaaggactta cattagtgac agtagcagga gctggtcatg aagtgcctct acaccgtccc    1320
cggcaagcct ttattctttt cagatccttt ttagagagca aaccaatgcc tatgacttga    1380

<210> SEQ ID NO 23
<211> LENGTH: 459
<212> TYPE: PRT
<213> ORGANISM: Arabidopsis thaliana
```

<400> SEQUENCE: 23

```
Met Asp Tyr Ser Phe Leu Leu Ile Ile Leu Leu Leu Thr Ile Ser Thr
  1               5                  10                  15

Ser Cys Cys Ala Ala Pro Ser Ser Tyr Val Glu Glu Gln Leu Arg Asp
             20                  25                  30

Arg Ile Ser Asn Leu Pro Gly Gln Pro Ser Asn Val Asp Phe Arg Gln
         35                  40                  45

Tyr Ser Gly Tyr Val Thr Val His Glu Glu Arg Gly Arg Ala Leu Phe
     50                  55                  60

Tyr Trp Leu Val Glu Ser Pro Leu Ala Arg Asp Pro Lys Ser Arg Pro
 65                  70                  75                  80

Leu Val Leu Trp Leu Asn Gly Gly Pro Gly Cys Ser Ser Val Ala Tyr
                 85                  90                  95

Gly Ala Ala Glu Glu Ile Gly Pro Phe Arg Val Gly Ser Asp Gly Lys
            100                 105                 110

Thr Leu His Ser Lys Leu Tyr Ala Trp Asn Lys Leu Ala Asn Leu Leu
        115                 120                 125

Phe Leu Glu Ser Pro Ala Gly Val Gly Phe Ser Tyr Ser Asn Thr Thr
    130                 135                 140

Ser Asp Leu Tyr Thr Thr Gly Asp Gln Arg Thr Ala Glu Asp Ser Tyr
145                 150                 155                 160

Ile Phe Leu Val Asn Trp Phe Glu Arg Phe Pro Gln Tyr Lys His Arg
                165                 170                 175

Glu Phe Tyr Ile Val Gly Glu Ser Tyr Ala Gly His Phe Val Pro Gln
            180                 185                 190

Leu Ser Lys Leu Val His Glu Arg Asn Lys Gly Phe Lys Asn Pro Ala
    195                 200                 205

Ile Asn Leu Lys Gly Phe Met Val Gly Asn Ala Val Thr Asp Asp Tyr
210                 215                 220

His Asp Tyr Ile Gly Thr Phe Glu Tyr Trp Asn His Gly Leu Ile
225                 230                 235                 240

Ser Asp Ser Thr Tyr His Gln Leu Lys Thr Ala Cys Tyr Ser Val Ser
                245                 250                 255

Ser Gln His Pro Ser Met Gln Cys Met Val Ala Leu Arg Asn Ala Glu
            260                 265                 270

Leu Glu Gln Gly Asn Ile Asp Pro Tyr Ser Ile Phe Thr Lys Pro Cys
    275                 280                 285

Asn Ser Thr Val Ala Leu Lys Arg Phe Leu Lys Gly Arg Tyr Pro Trp
290                 295                 300

Met Ser Arg Ala Tyr Asp Pro Cys Thr Glu Arg Tyr Ser Asn Val Tyr
305                 310                 315                 320

Phe Asn Arg Leu Asp Val Gln Lys Ala Leu His Ala Asn Val Thr Arg
                325                 330                 335

Leu Ser Tyr Pro Trp Lys Ala Cys Ser Asp Ile Val Gly Ser Tyr Trp
            340                 345                 350

Asp Asp Ser Pro Leu Ser Met Leu Pro Ile Tyr Lys Glu Leu Ile Thr
    355                 360                 365

Ala Gly Leu Lys Ile Trp Val Phe Ser Gly Asp Thr Asp Ala Val Val
370                 375                 380

Pro Ile Thr Ala Thr Arg Tyr Ser Val Asp Ala Leu Lys Leu Ala Thr
385                 390                 395                 400

Ile Thr Asn Trp Tyr Pro Trp Tyr Asp His Gly Lys Val Gly Gly Trp
                405                 410                 415
```

Ser Gln Val Tyr Lys Gly Leu Thr Leu Val Thr Val Ala Gly Ala Gly
        420                 425                 430

His Glu Val Pro Leu His Arg Pro Arg Gln Ala Phe Ile Leu Phe Arg
        435                 440                 445

Ser Phe Leu Glu Ser Lys Pro Met Pro Met Thr
        450                 455

<210> SEQ ID NO 24
<211> LENGTH: 1473
<212> TYPE: DNA
<213> ORGANISM: Oryza sativa

<400> SEQUENCE: 24

```
atggcggcgg ccgccgtgct cctggccgcc atcctactgg cgctgtcccc tctccccatg      60
tccctctccg ccggcggcgg cggcggaggt gacactggca cggccgaggc ggccgcggac     120
cgaatcacgg ccctgccggg gcagccacgg gtcaacttct ccatgtactc cgggtacgtc     180
accgtcgacg cggccgccgg gcgcgcgctc ttctactggc tcatcgaggc cgccgacccg     240
gcgtccgcgc cgctcgtgct ctggctcaac ggcgggccgg gtgctcctc cgttgggtac      300
ggcgcgtccg aggagctcgg cgcgttccgg atcaaccccg acgggaggtc gctctacttg     360
aaccccctacc cctggaacag agtggccaac atgctgttct ggactcccc cgccggcgtc     420
ggctactcct actccaacac cacctccgat ctgttcactg ctggtgataa caagacagct     480
catgattcat atgctttctt ggtgaattgg ttggaacggt ttccgcagta caagtaccgt     540
gatttctaca tcgcaggcga gagctatgga gggcactatg tccctcagtt gtctcagcta     600
gtgtaccgga ataacaaaga cgttgaaaag cctatcctaa actttaaagg ctttatggtt     660
ggaaatgcgg taatcgatga ttaccatgac tacgttggca catttgagta ctggtggaca     720
cacgggctga tatctgatga tacatatcag aagctgcagg tggcctgtga ttttgaatca     780
tctgctcacg catcagaagc atgtaacaag atttatgaag tggctgaggc tgaacaaggg     840
aacattgatg catacagcat ctatacgcct acctgtaaaa aaacttcatt tctcaaacgc     900
aggttaataa ggggtaactc gccatggttg cctagaggat atgatccctg cactgaaaag     960
tactctacga agtactacaa cctaccagaa gtgcaaaaag catttcatgc caatgtcact    1020
ggaataccgt atgcctggac cacctgcagt gatgacttgt tttattattg gaaagattca    1080
ccaaggtcca tgcttcctat ttaccgtgag ctgattgcgg ctggtctaag aatatgggtt    1140
ttcagcggcg acgctgattc tgtagtcccc ctcactgcga caagatactc cattgatgca    1200
ctctatctac ctactgtcac taactggtat ccttggtatg atgatgagga ggttgctggt    1260
tggtgtcaag tgtatcaagg tttgacactg gtgacgatcc gaggagcagg gcatgaagtt    1320
cctctccatc gtccacggca agccttaaaa ctctttgagc atttcctaca agataagccc    1380
atgcctcaac tgagtatac ggccgagaac ttgacgaacg agagctgcta ctgctactgc    1440
ttagtgctag ctcttgatca gcctgaacat tga                                1473
```

<210> SEQ ID NO 25
<211> LENGTH: 490
<212> TYPE: PRT
<213> ORGANISM: Oryza sativa

<400> SEQUENCE: 25

Met Ala Ala Ala Ala Val Leu Leu Ala Ala Ile Leu Leu Ala Leu Ser
  1               5                  10                  15

-continued

```
Pro Leu Pro Met Ser Leu Ser Ala Gly Gly Gly Gly Asp Thr
            20              25              30
Gly Thr Ala Glu Ala Ala Ala Asp Arg Ile Thr Ala Leu Pro Gly Gln
         35              40              45
Pro Arg Val Asn Phe Ser Met Tyr Ser Gly Tyr Val Thr Val Asp Ala
     50              55              60
Ala Ala Gly Arg Ala Leu Phe Tyr Trp Leu Ile Glu Ala Ala Asp Pro
65              70              75              80
Ala Ser Ala Pro Leu Val Leu Trp Leu Asn Gly Gly Pro Gly Cys Ser
                 85              90              95
Ser Val Gly Tyr Gly Ala Ser Glu Glu Leu Gly Ala Phe Arg Ile Asn
             100             105             110
Pro Asp Gly Arg Ser Leu Tyr Leu Asn Pro Tyr Pro Trp Asn Arg Val
             115             120             125
Ala Asn Met Leu Phe Leu Asp Ser Pro Ala Gly Val Gly Tyr Ser Tyr
         130             135             140
Ser Asn Thr Thr Ser Asp Leu Phe Thr Ala Gly Asp Asn Lys Thr Ala
145             150             155             160
His Asp Ser Tyr Ala Phe Leu Val Asn Trp Leu Glu Arg Phe Pro Gln
                 165             170             175
Tyr Lys Tyr Arg Asp Phe Tyr Ile Ala Gly Glu Ser Tyr Gly Gly His
             180             185             190
Tyr Val Pro Gln Leu Ser Gln Leu Val Tyr Arg Asn Asn Lys Asp Val
             195             200             205
Glu Lys Pro Ile Leu Asn Phe Lys Gly Phe Met Val Gly Asn Ala Val
    210             215             220
Ile Asp Asp Tyr His Asp Tyr Val Gly Thr Phe Glu Tyr Trp Trp Thr
225             230             235             240
His Gly Leu Ile Ser Asp Asp Thr Tyr Gln Lys Leu Gln Val Ala Cys
                 245             250             255
Asp Phe Glu Ser Ser Ala His Ala Ser Glu Ala Cys Asn Lys Ile Tyr
             260             265             270
Glu Val Ala Glu Ala Glu Gln Gly Asn Ile Asp Ala Tyr Ser Ile Tyr
             275             280             285
Thr Pro Thr Cys Lys Lys Thr Ser Phe Leu Lys Arg Arg Leu Ile Arg
        290             295             300
Gly Asn Ser Pro Trp Leu Pro Arg Gly Tyr Asp Pro Cys Thr Glu Lys
305             310             315             320
Tyr Ser Thr Lys Tyr Tyr Asn Leu Pro Glu Val Gln Lys Ala Phe His
                 325             330             335
Ala Asn Val Thr Gly Ile Pro Tyr Ala Trp Thr Thr Cys Ser Asp Asp
             340             345             350
Leu Phe Tyr Tyr Trp Lys Asp Ser Pro Arg Ser Met Leu Pro Ile Tyr
             355             360             365
Arg Glu Leu Ile Ala Ala Gly Leu Arg Ile Trp Val Phe Ser Gly Asp
    370             375             380
Ala Asp Ser Val Val Pro Leu Thr Ala Thr Arg Tyr Ser Ile Asp Ala
385             390             395             400
Leu Tyr Leu Pro Thr Val Thr Asn Trp Tyr Pro Trp Tyr Asp Asp Glu
                 405             410             415
Glu Val Ala Gly Trp Cys Gln Val Tyr Gln Gly Leu Thr Leu Val Thr
             420             425             430
Ile Arg Gly Ala Gly His Glu Val Pro Leu His Arg Pro Arg Gln Ala
```

-continued

```
                  435                 440                 445
Leu Lys Leu Phe Glu His Phe Leu Gln Asp Lys Pro Met Pro Gln Pro
    450                 455                 460

Glu Tyr Thr Ala Glu Asn Leu Thr Asn Glu Ser Cys Tyr Cys Tyr Cys
465                 470                 475                 480

Leu Val Leu Ala Leu Asp Gln Pro Glu His
                485                 490

<210> SEQ ID NO 26
<211> LENGTH: 1161
<212> TYPE: DNA
<213> ORGANISM: Oryza sativa

<400> SEQUENCE: 26
atgtcatgtc ctggatgctc atcgattgcg tatggagcat ctgaagagat tgggcccattt      60 aggattaaga caaacgggac agggctctat ctgaacaagt actcatgaa cagagaggca      120 aacctcctgt tcctggaatc acctgccgga gttggctttt catactccaa caccacctct      180
gatctcaaga catctggtga tgagaggaca gctcaagatg cgttgcagtt cttgatcagt      240
tggatgtccc gcttcccaca gtatcggcac cgggatttct acattgctgg agaaagctat      300
gctggacatt acgttcccca gttggcaagg aagatcgttg agttcaacaa ggcctcacca      360
tatcctttca tcaacctcaa ggggatcctt gtgggcaatg gggtgactga caactactac      420
gacaacatcg gcacggtgac ctactggtgg acgcacgcca tgatctcgga caccacctac      480
aaggccatca tgtcgtcgtg caacttcacc agcgccaacg tctccaggct ctgcaaccgc      540
gccatgagct acgccatgaa ccacgagttc ggcgacatcg accagtacag catctacacg      600
ccgtcctgcg ccgccgccgc cgccgccaac gccaccggcc gccgccgcgg caaggccgcc      660
gtgctgaggt tcaaggacac cttcctacgg cgccggtcgt tcggctacga ccccgcacg      720 gagacatacg ccgagaagta ctacaaccgg ccggatgttc agaaggccat gcatgccaac      780
atcactggga ttccttacag atggacagcc tgcagtgatg tgctcatcaa gacgtggcga      840
gattcagagt tctccatgct gccgacttac aagttgctga tgaaggccgg gctgaggata      900
tgggtgttca gtggcgacac ggattcagtc gttccggtta ctgcaacgag gtttgcgctt      960
agccatcttg gactgaagac gaagatccgc tggtacccctt ggtactcagc tggacaggtt      1020
ggaggatggt ctgaggtgta tgaagggctc acatttgcgt cagtgagagg tgctgggcat      1080
gaggtgccac tgtttcagcc aaggagagca ttcaggatgt ttcagtcgtt cttggcaggg      1140
gagccattgc caaaatcctg a                                                1161

<210> SEQ ID NO 27
<211> LENGTH: 386
<212> TYPE: PRT
<213> ORGANISM: Oryza sativa

<400> SEQUENCE: 27

Met Ser Cys Pro Gly Cys Ser Ser Ile Ala Tyr Gly Ala Ser Glu Glu
 1               5                  10                  15

Ile Gly Pro Phe Arg Ile Lys Thr Asn Gly Thr Gly Leu Tyr Leu Asn
            20                  25                  30

Lys Tyr Ser Trp Asn Arg Glu Ala Asn Leu Leu Phe Leu Glu Ser Pro
        35                  40                  45

Ala Gly Val Gly Phe Ser Tyr Ser Asn Thr Thr Ser Asp Leu Lys Thr
    50                  55                  60
```

Ser Gly Asp Glu Arg Thr Ala Gln Asp Ala Leu Gln Phe Leu Ile Ser
 65                  70                  75                  80

Trp Met Ser Arg Phe Pro Gln Tyr Arg His Arg Asp Phe Tyr Ile Ala
             85                  90                  95

Gly Glu Ser Tyr Ala Gly His Tyr Val Pro Gln Leu Ala Arg Lys Ile
        100                 105                 110

Val Glu Phe Asn Lys Ala Ser Pro Tyr Pro Phe Ile Asn Leu Lys Gly
    115                 120                 125

Ile Leu Val Gly Asn Gly Val Thr Asp Asn Tyr Tyr Asp Asn Ile Gly
    130                 135                 140

Thr Val Thr Tyr Trp Trp Thr His Ala Met Ile Ser Asp Thr Thr Tyr
145                 150                 155                 160

Lys Ala Ile Met Ser Ser Cys Asn Phe Thr Ser Ala Asn Val Ser Arg
                165                 170                 175

Leu Cys Asn Arg Ala Met Ser Tyr Ala Met Asn His Glu Phe Gly Asp
            180                 185                 190

Ile Asp Gln Tyr Ser Ile Tyr Thr Pro Ser Cys Ala Ala Ala Ala Ala
        195                 200                 205

Ala Asn Ala Thr Gly Arg Arg Gly Lys Ala Ala Val Leu Arg Phe
    210                 215                 220

Lys Asp Thr Phe Leu Arg Arg Ser Phe Gly Tyr Asp Pro Cys Thr
225                 230                 235                 240

Glu Thr Tyr Ala Glu Lys Tyr Tyr Asn Arg Pro Asp Val Gln Lys Ala
                245                 250                 255

Met His Ala Asn Ile Thr Gly Ile Pro Tyr Arg Trp Thr Ala Cys Ser
            260                 265                 270

Asp Val Leu Ile Lys Thr Trp Arg Asp Ser Glu Phe Ser Met Leu Pro
        275                 280                 285

Thr Tyr Lys Leu Leu Met Lys Ala Gly Leu Arg Ile Trp Val Phe Ser
    290                 295                 300

Gly Asp Thr Asp Ser Val Val Pro Val Thr Ala Thr Arg Phe Ala Leu
305                 310                 315                 320

Ser His Leu Gly Leu Lys Thr Lys Ile Arg Trp Tyr Pro Trp Tyr Ser
                325                 330                 335

Ala Gly Gln Val Gly Gly Trp Ser Glu Val Tyr Glu Gly Leu Thr Phe
            340                 345                 350

Ala Ser Val Arg Gly Ala Gly His Glu Val Pro Leu Phe Gln Pro Arg
        355                 360                 365

Arg Ala Phe Arg Met Phe Gln Ser Phe Leu Ala Gly Glu Pro Leu Pro
370                 375                 380

Lys Ser
385

<210> SEQ ID NO 28
<211> LENGTH: 1458
<212> TYPE: DNA
<213> ORGANISM: Oryza sativa

<400> SEQUENCE: 28
atggccggcg ctaccgctgc cgccgtctcc tcctccttcc tcgcgctcgc gttgctctcg     60
ctctgcgccg cggccgctgg cggctcgcct cagctggacg cggaggccgc gcggcagcag    120
gaggccgacc gcgtgacgag gctgccgggg caacccgccg tgcggttcgc gcagtacgcc    180
gggtacgtga cggtgaacga gacgcacggc cgcgcgctct tctactggtt cttcgaggcc    240

```
accgccgccg ccgacaagaa gcccctcgtc ctctggctca acggcgggcc tgggtgttcg      300
tctgttgggt atggagaagc ggaggagctc ggtccattct tggtgcagaa gggcaagccg      360
gagctaaaat ggaacaagta ctcgtggaac aaagaggcca atctgatgtt cctggagtcc      420
cctgtgggtg tcggcttctc atacactaac acaagctccg atctgcagca gcttggcgac      480
aagatcaccg ctgatgatgc ttacatcttc ctgctcaact ggttcaagcg cttccctcag      540
tacaaatctc acgacttcta catcgctgga gagagctacg ctgggcatta cgttccacag      600
ctttcggaga agattttcga cggcaacaag caaggcccca aggagaacta catcaacttc      660
aagggtttca tgatagggaa tgccctgatg acgacgagga cggaccagac gggcatgatc      720
gactacgcct gggaccacgc cgtcatctcg gaccgggtgt acgccgacgt caagaagtac      780
tgcaacttca gcatggagaa cgtgaccgac gcgtgcgaca cgcgcgctca cgagtacttc      840
gccgtgtacc gcctcatcga catgtacagc ctctacaccc ccgtctgcac cgaggtctcg      900
tcgtcggcgg cgttcggcca gcgccaggtc gccgtccacg cgccgccccc aaaaatcttc      960
tccaaatacc atgggtggta catgaggccg gcggggtacg atccgtgcac gtcggatcac      1020
gccgaggtgt acttcaaccg ggctgacgtg caggaggcgc tgcacgccaa cgtgaccaat      1080
atcggctaca actggacgca ctgcagcgac gtgatcggca agtggagaga tgctcccttc      1140
tcgactctcc ccatcatccg taagctcgtc gccggcggca tcagggtctg gttttcagc      1200 ggtgacaccg atggaaggat ccccgtgacg tcgacgaggc tcaccctgaa caagcttggg      1260
ctgaagacgt gcaggagtg gacgccgtgg tacgaccatc agcaggttgg aggatggacg      1320
atcctctacg agggcctgac gttcgtgacg atccgcggcg ccgggcacga ggttcccctg      1380
cacgcgccga ggcaggcgct cagcctcttc agccacttct ggctgacaa gaagatgcct      1440 ccgacggcgt tcccctag                                                   1458

<210> SEQ ID NO 29
<211> LENGTH: 485
<212> TYPE: PRT
<213> ORGANISM: Oryza sativa

<400> SEQUENCE: 29

Met Ala Gly Ala Thr Ala Ala Val Ser Ser Phe Leu Ala Leu
1               5                   10                  15

Ala Leu Leu Ser Leu Cys Ala Ala Ala Gly Gly Ser Pro Gln Leu
                20                  25                  30

Asp Ala Glu Ala Ala Arg Gln Gln Glu Ala Asp Arg Val Thr Arg Leu
        35                  40                  45

Pro Gly Gln Pro Ala Val Arg Phe Ala Gln Tyr Ala Gly Tyr Val Thr
    50                  55                  60

Val Asn Glu Thr His Gly Arg Ala Leu Phe Tyr Trp Phe Phe Glu Ala
65                  70                  75                  80

Thr Ala Ala Asp Lys Lys Pro Leu Val Leu Trp Leu Asn Gly Gly
                85                  90                  95

Pro Gly Cys Ser Ser Val Gly Tyr Gly Glu Ala Glu Glu Leu Gly Pro
            100                 105                 110

Phe Leu Val Gln Lys Gly Lys Pro Glu Leu Lys Trp Asn Lys Tyr Ser
        115                 120                 125

Trp Asn Lys Glu Ala Asn Leu Met Phe Leu Glu Ser Pro Val Gly Val
    130                 135                 140

Gly Phe Ser Tyr Thr Asn Thr Ser Ser Asp Leu Gln Gln Leu Gly Asp
145                 150                 155                 160
```

```
Lys Ile Thr Ala Asp Asp Ala Tyr Ile Phe Leu Leu Asn Trp Phe Lys
                165                 170                 175
Arg Phe Pro Gln Tyr Lys Ser His Asp Phe Tyr Ile Ala Gly Glu Ser
            180                 185                 190
Tyr Ala Gly His Tyr Val Pro Gln Leu Ser Glu Lys Ile Phe Asp Gly
        195                 200                 205
Asn Lys Gln Gly Pro Lys Glu Asn Tyr Ile Asn Phe Lys Gly Phe Met
    210                 215                 220
Ile Gly Asn Ala Leu Met Asp Asp Glu Thr Asp Gln Thr Gly Met Ile
225                 230                 235                 240
Asp Tyr Ala Trp Asp His Ala Val Ile Ser Asp Arg Val Tyr Ala Asp
                245                 250                 255
Val Lys Lys Tyr Cys Asn Phe Ser Met Glu Asn Val Thr Asp Ala Cys
            260                 265                 270
Asp Ser Ala Leu Thr Glu Tyr Phe Ala Val Tyr Arg Leu Ile Asp Met
        275                 280                 285
Tyr Ser Leu Tyr Thr Pro Val Cys Thr Glu Val Ser Ser Ser Ala Ala
    290                 295                 300
Phe Gly Gln Arg Gln Val Ala Val His Gly Ala Ala Pro Lys Ile Phe
305                 310                 315                 320
Ser Lys Tyr His Gly Trp Tyr Met Arg Pro Ala Gly Tyr Asp Pro Cys
                325                 330                 335
Thr Ser Asp His Ala Glu Val Tyr Phe Asn Arg Ala Asp Val Gln Glu
            340                 345                 350
Ala Leu His Ala Asn Val Thr Asn Ile Gly Tyr Asn Trp Thr His Cys
        355                 360                 365
Ser Asp Val Ile Gly Lys Trp Arg Asp Ala Pro Phe Ser Thr Leu Pro
    370                 375                 380
Ile Ile Arg Lys Leu Val Ala Gly Gly Ile Arg Val Trp Val Phe Ser
385                 390                 395                 400
Gly Asp Thr Asp Gly Arg Ile Pro Val Thr Ser Thr Arg Leu Thr Leu
                405                 410                 415
Asn Lys Leu Gly Leu Lys Thr Val Gln Glu Trp Thr Pro Trp Tyr Asp
            420                 425                 430
His Gln Gln Val Gly Gly Trp Thr Ile Leu Tyr Glu Gly Leu Thr Phe
        435                 440                 445
Val Thr Ile Arg Gly Ala Gly His Glu Val Pro Leu His Ala Pro Arg
    450                 455                 460
Gln Ala Leu Ser Leu Phe Ser His Phe Leu Ala Asp Lys Lys Met Pro
465                 470                 475                 480
Pro Thr Ala Phe Pro
                485

<210> SEQ ID NO 30
<211> LENGTH: 1449
<212> TYPE: DNA
<213> ORGANISM: Oryza sativa

<400> SEQUENCE: 30
atgaaggttc agacttcgtc accttgcttg ctactcctac ttggctctct tgcactggtt      60
acactgacac tgtgtggccc agctgcttct gcacggcctg aaacgggcag cctcgatgca     120
tcagccacgg cggccatgga gttgcaggag ctcgaccgcg tgatgtcgct gcccgggcag     180
ccggcctact cgccggaatt caggcaatac tccggctatg tcaccactga cgagtacctt     240
```

```
ggcaaggcac tcttctactg gttcttggag gccactgaca agcctgacga gaagccactc      300
gtcttgtggc taaatggagg acctggatgt tcttccattg ggtttggaca ggcacaggag      360
ctagggccat ttctggtgaa gaaagatgtg gctgaacttg agctgaatcc atacgcatgg      420
aaccaagttg ccaatttgct gttcctggac tctcctgctg gtgttgggtt ttcttacacc      480
aacacatcct ttggaaaaga tccaccagga gacaattcca ccgcatatgg ttcatacact      540
ttcctgatca ggtggttcca gaggttccct cagcacaaaa tgaaggagtt ctacatagct      600
ggagagagct atgcaggaca ttacgttccc cagcttgcta atgtgattgt ggatcagaac      660
aagattgcac ctaaagaaaa ttatataaac ttgaaaggca tcatgatagg aaatgcttac      720
atggatggtg acacggattt gctaggaatt gttgattctg catggcatca cgcactcatc      780
tcagacaaac tttacagtga cttccagaag ttctgcaact tcagtttggt tgatctgtct      840
aaagagtgca acgctgcaat cgatcagttc aacgctctct acagcatcat agatatctac      900
agcctttaca ccctcgatg cgagctcgga tacccaaact tcaactcgtc gtttgcagca      960
caaatcggac ggaccagcag ccgtatacca atgggctatg atccatgctc gcaaacgtac     1020
gcgactgaat atttcaaccg taaagatgtt cagaaagctc tgcatgccaa tatccctgga     1080
gcatactccc tttgccataa ttctatcaac cgagcatgga acgactctga catgactgtc     1140
cttccaatcg tcaagaaact cactcaatca gggctccgga tatggattta cagcggcgac     1200
acggacgcaa gaatccctac aacctcaacc aggtacacgc tgaaaaagct tggcctgccc     1260
atcaaagagg actggtcgcc atggttccat cacaagcagg ttggtgggtg gagtgtggtg     1320
ttcgacggac tgacatttgt cacggtgaga ggagccggcc acatggtgcc atccatcatg     1380
ccagagcaag cgcttgagct gttcaagtac ttcctggcca atcagaacct cccatccaag     1440
ccattctag                                                             1449
```

<210> SEQ ID NO 31
<211> LENGTH: 482
<212> TYPE: PRT
<213> ORGANISM: Oryza sativa

<400> SEQUENCE: 31

Met Lys Val Gln Thr Ser Ser Pro Cys Leu Leu Leu Leu Gly Ser
 1               5                  10                  15

Leu Ala Leu Val Thr Leu Thr Leu Cys Gly Pro Ala Ala Ser Ala Arg
            20                  25                  30

Pro Glu Thr Gly Ser Leu Asp Ala Ser Ala Thr Ala Ala Met Glu Leu
        35                  40                  45

Gln Glu Leu Asp Arg Val Met Ser Leu Pro Gly Gln Pro Ala Tyr Ser
    50                  55                  60

Pro Glu Phe Arg Gln Tyr Ser Gly Tyr Val Thr Thr Asp Glu Tyr Leu
65                  70                  75                  80

Gly Lys Ala Leu Phe Tyr Trp Phe Leu Glu Ala Thr Asp Lys Pro Asp
                85                  90                  95

Glu Lys Pro Leu Val Leu Trp Leu Asn Gly Gly Pro Gly Cys Ser Ser
            100                 105                 110

Ile Gly Phe Gly Gln Ala Gln Glu Leu Gly Pro Phe Leu Val Lys Lys
        115                 120                 125

Asp Val Ala Glu Leu Glu Leu Asn Pro Tyr Ala Trp Asn Gln Val Ala
    130                 135                 140

Asn Leu Leu Phe Leu Asp Ser Pro Ala Gly Val Gly Phe Ser Tyr Thr

```
                145                 150                 155                 160
Asn Thr Ser Phe Gly Lys Asp Pro Pro Gly Asp Asn Ser Thr Ala Tyr
                165                 170                 175
Gly Ser Tyr Thr Phe Leu Ile Arg Trp Phe Gln Arg Phe Pro Gln His
                180                 185                 190
Lys Met Lys Glu Phe Tyr Ile Ala Gly Glu Ser Tyr Ala Gly His Tyr
                195                 200                 205
Val Pro Gln Leu Ala Asn Val Ile Val Asp Gln Asn Lys Ile Ala Pro
                210                 215                 220
Lys Glu Asn Tyr Ile Asn Leu Lys Gly Ile Met Ile Gly Asn Ala Tyr
225                 230                 235                 240
Met Asp Gly Asp Thr Asp Leu Leu Gly Ile Val Asp Ser Ala Trp His
                245                 250                 255
His Ala Leu Ile Ser Asp Lys Leu Tyr Ser Asp Phe Gln Lys Phe Cys
                260                 265                 270
Asn Phe Ser Leu Val Asp Leu Ser Lys Glu Cys Asn Ala Ala Ile Asp
                275                 280                 285
Gln Phe Asn Ala Leu Tyr Ser Ile Ile Asp Ile Tyr Ser Leu Tyr Thr
                290                 295                 300
Pro Arg Cys Glu Leu Gly Tyr Pro Asn Phe Asn Ser Ser Phe Ala Ala
305                 310                 315                 320
Gln Ile Gly Arg Thr Ser Ser Arg Ile Pro Met Gly Tyr Asp Pro Cys
                325                 330                 335
Ser Gln Thr Tyr Ala Thr Glu Tyr Phe Asn Arg Lys Asp Val Gln Lys
                340                 345                 350
Ala Leu His Ala Asn Ile Pro Gly Ala Tyr Ser Leu Cys His Asn Ser
                355                 360                 365
Ile Asn Arg Ala Trp Asn Asp Ser Asp Met Thr Val Leu Pro Ile Val
                370                 375                 380
Lys Lys Leu Thr Gln Ser Gly Leu Arg Ile Trp Ile Tyr Ser Gly Asp
385                 390                 395                 400
Thr Asp Ala Arg Ile Pro Thr Thr Ser Thr Arg Tyr Thr Leu Lys Lys
                405                 410                 415
Leu Gly Leu Pro Ile Lys Glu Asp Trp Ser Pro Trp Phe His His Lys
                420                 425                 430
Gln Val Gly Gly Trp Ser Val Val Phe Asp Gly Leu Thr Phe Val Thr
                435                 440                 445
Val Arg Gly Ala Gly His Met Val Pro Ser Ile Met Pro Glu Gln Ala
                450                 455                 460
Leu Glu Leu Phe Lys Tyr Phe Leu Ala Asn Gln Asn Leu Pro Ser Lys
465                 470                 475                 480
Pro Phe

<210> SEQ ID NO 32
<211> LENGTH: 1314
<212> TYPE: DNA
<213> ORGANISM: Oryza sativa

<400> SEQUENCE: 32
atggagttgc aggagctcga ccgcgtgatg tcgctgcccg ggcagccggc ctactcgccg      60
gaattcaggc aatactccgg ctatgtcacc actgacgagt accttggcaa ggcactcttc     120
tactggttct tggaggccac tgacaagcct gacgagaagc cactcgtctt gtggctaaat     180
ggaggacctg gatgttcttc cattgggttt ggacaggcac aggagctagg gccatttctg     240
```

```
gtgaagaaag atgtggctga acttgagctg aatccatacg catggaacca agttgccaat      300
ttgctgttcc tggactctcc tgctggtgtt gggttttctt acaccaacac atcctttgga      360
aaagatccac caggagacaa ttccaccgca tatggttcat acactttcct gatcaggtgg      420
ttccagaggt tccctcagca caaaatgaag gagttctaca tagctggaga gagctatgca      480
ggacattacg ttccccagct tgctaatgtg attgtggatc agaacaagat tgcacctaaa      540
gaaaattata taaacttgaa aggcatcatg ataggaaatg cttacatgga tggtgacacg      600
gatttgctag gaattgttga ttctgcatgg catcacgcac tcatctcaga caaactttac      660
agtgactttc agaagttctg caacttcagt ttggttgatc tgtctaaaga gtgcaacgct      720
gcaatcgatc agttcaacgc tctctacagc atcatagata tctacagcct ttacacccct      780
cgatgcgagc tcggataccc aaacttcaac tcgtcgtttg cagcacaaat cggacggacc      840
agcagccgta taccaatggg ctatgatcca tgctcgcaaa cgtacgcgac tgaatatttc      900
aaccgtaaag atgttcagaa agctctgcat gccaatatcc ctggagcata ctcccttttgc      960 cataattcta tcaaccgagc atggaacgac tctgacatga ctgtccttcc aatcgtcaag     1020
aaactcactc aatcagggct ccggatatgg atttacagcg gcgacacgga cgcaagaatc     1080
cctacaacct caaccaggta cacgctgaaa aagcttggcc tgcccatcaa agaggactgg     1140
tcgccatggt tccatcacaa gcaggttggt gggtggagtg tggtgttcga cggactgaca     1200
tttgtcacgg tgagaggagc cggccacatg gtgccatcca tcatgccaga gcaagcgctt     1260
gagctgttca gtacttcct ggccaatcag aacctcccat ccaagccatt ctag             1314
```

<210> SEQ ID NO 33  
<211> LENGTH: 437  
<212> TYPE: PRT  
<213> ORGANISM: Oryza sativa
<400> SEQUENCE: 33

```
Met Glu Leu Gln Glu Leu Asp Arg Val Met Ser Leu Pro Gly Gln Pro
 1               5                  10                  15

Ala Tyr Ser Pro Glu Phe Arg Gln Tyr Ser Gly Tyr Val Thr Thr Asp
            20                  25                  30

Glu Tyr Leu Gly Lys Ala Leu Phe Tyr Trp Phe Leu Glu Ala Thr Asp
        35                  40                  45

Lys Pro Asp Glu Lys Pro Leu Val Leu Trp Leu Asn Gly Gly Pro Gly
    50                  55                  60

Cys Ser Ser Ile Gly Phe Gly Gln Ala Gln Glu Leu Gly Pro Phe Leu
65                  70                  75                  80

Val Lys Lys Asp Val Ala Glu Leu Glu Leu Asn Pro Tyr Ala Trp Asn
                85                  90                  95

Gln Val Ala Asn Leu Leu Phe Leu Asp Ser Pro Ala Gly Val Gly Phe
            100                 105                 110

Ser Tyr Thr Asn Thr Ser Phe Gly Lys Asp Pro Pro Gly Asp Asn Ser
        115                 120                 125

Thr Ala Tyr Gly Ser Tyr Thr Phe Leu Ile Arg Trp Phe Gln Arg Phe
    130                 135                 140

Pro Gln His Lys Met Lys Glu Phe Tyr Ile Ala Gly Glu Ser Tyr Ala
145                 150                 155                 160

Gly His Tyr Val Pro Gln Leu Ala Asn Val Ile Val Asp Gln Asn Lys
                165                 170                 175

Ile Ala Pro Lys Glu Asn Tyr Ile Asn Leu Lys Gly Ile Met Ile Gly
```

```
                        180                     185                     190
Asn Ala Tyr Met Asp Gly Asp Thr Asp Leu Leu Gly Ile Val Asp Ser
            195                     200                     205

Ala Trp His His Ala Leu Ile Ser Asp Lys Leu Tyr Ser Asp Phe Gln
            210                     215                     220

Lys Phe Cys Asn Phe Ser Leu Val Asp Leu Ser Lys Glu Cys Asn Ala
225                     230                     235                     240

Ala Ile Asp Gln Phe Asn Ala Leu Tyr Ser Ile Ile Asp Ile Tyr Ser
                    245                     250                     255

Leu Tyr Thr Pro Arg Cys Glu Leu Gly Tyr Pro Asn Phe Asn Ser Ser
            260                     265                     270

Phe Ala Ala Gln Ile Gly Arg Thr Ser Ser Arg Ile Pro Met Gly Tyr
            275                     280                     285

Asp Pro Cys Ser Gln Thr Tyr Ala Thr Glu Tyr Phe Asn Arg Lys Asp
            290                     295                     300

Val Gln Lys Ala Leu His Ala Asn Ile Pro Gly Ala Tyr Ser Leu Cys
305                     310                     315                     320

His Asn Ser Ile Asn Arg Ala Trp Asn Asp Ser Asp Met Thr Val Leu
                    325                     330                     335

Pro Ile Val Lys Lys Leu Thr Gln Ser Gly Leu Arg Ile Trp Ile Tyr
                    340                     345                     350

Ser Gly Asp Thr Asp Ala Arg Ile Pro Thr Thr Ser Thr Arg Tyr Thr
            355                     360                     365

Leu Lys Lys Leu Gly Leu Pro Ile Lys Glu Asp Trp Ser Pro Trp Phe
    370                     375                     380

His His Lys Gln Val Gly Gly Trp Ser Val Val Phe Asp Gly Leu Thr
385                     390                     395                     400

Phe Val Thr Val Arg Gly Ala Gly His Met Val Pro Ser Ile Met Pro
                    405                     410                     415

Glu Gln Ala Leu Glu Leu Phe Lys Tyr Phe Leu Ala Asn Gln Asn Leu
            420                     425                     430

Pro Ser Lys Pro Phe
            435
```